US012065663B2

(12) United States Patent
Yang et al.

(10) Patent No.: US 12,065,663 B2
(45) **Date of Patent: *Aug. 20, 2024**

(54) VECTOR AND METHOD FOR TREATING BIETTI'S CRYSTALLINE DYSTROPHY

(71) Applicant: CHIGENOVO CO., LTD, Beijing (CN)

(72) Inventors: Liping Yang, Beijing (CN); Shaohong Chen, Beijing (CN); Ruixuan Jia, Beijing (CN); Fan Zhang, Beijing (CN); Saichao He, Beijing (CN); Tianyong Shi, Beijing (CN); Dandan Hao, Beijing (CN); Hongjie Pei, Beijing (CN); Luying Zeng, Beijing (CN)

(73) Assignee: CHIGENOVO CO., LTD, Beijing (CN)

( * ) Notice: Subject to any disclaimer, the term of this patent is extended or adjusted under 35 U.S.C. 154(b) by 16 days.

This patent is subject to a terminal disclaimer.

(21) Appl. No.: 17/812,425

(22) Filed: Jul. 13, 2022

(65) Prior Publication Data

US 2024/0018541 A1 Jan. 18, 2024

(51) Int. Cl.

*C12N 15/86* (2006.01)
*A61K 48/00* (2006.01)
*A61P 27/02* (2006.01)
*C12N 9/02* (2006.01)

(52) U.S. Cl.

CPC .............. *C12N 15/86* (2013.01); *A61P 27/02* (2018.01); *C12N 9/0071* (2013.01); *A61K 48/00* (2013.01); *C12N 2750/14143* (2013.01)

(58) Field of Classification Search

None

See application file for complete search history.

(56) References Cited

FOREIGN PATENT DOCUMENTS

CN 111733174 A * 10/2020 ............. A61K 38/18

OTHER PUBLICATIONS

Gregory A. Wray, Matthew W. Hahn, Ehab Abouheif, James P. Balhoff, Margaret Pizer, Matthew V. Rockman, Laura A. Romano, The Evolution of Transcriptional Regulation in Eukaryotes, Molecular Biology and Evolution, vol. 20, Issue 9, Sep. 2003, pp. 1377-1419, https://doi.org/10.1093/molbev/msg140 (Year: 2003).*

Jiao, X., Li, A., Jin, ZB. et al. Identification and population history of CYP4V2 mutations in patients with Bietti crystalline corneoretinal dystrophy. Eur J Hum Genet 25, 461-471 (2017). https://doi.org/10.1038/ejhg.2016.184 (Year: 2017).*

Qu, B., Wu, S., Jiao, G. et al. Treating Bietti crystalline dystrophy in a high-fat diet-exacerbated murine model using gene therapy. Gene Ther 27, 370-382 (2020). https://doi.org/10.1038/s41434-020-0159-3 (Year: 2020).*

Nelson et al. Comparison of cytochrome P450 (CYP) genes from the mouse and human genomes, including nomenclature recommendations for genes, pseudogenes and alternative-splice variants. Pharmacogenetics 14(1):p. 1-18, Jan. 2004. (Year: 2004).*

Norrman K, Fischer Y, Bonnamy B, Wolfhagen Sand F, Ravassard P, Semb H. Quantitative comparison of constitutive promoters in human ES cells. PLoS One. Aug. 26, 2010;5(8): e12413. doi: 10.1371/journal.pone.0012413. PMID: 20865032; PMCID: PMC2928720. (Year: 2010).*

Lin J, Nishiguchi KM, Nakamura M, Dryja TP, Berson EL, Miyake Y. Recessive mutations in the CYP4V2 gene in East Asian and Middle Eastern patients with Bietti crystalline corneoretinal dystrophy. J Med Genet. Jun. 2005;42(6):e38. doi: 10.1136/jmg.2004.029066. PMID: 15937078; PMCID: PMC1736086. (Year: 2004).*

Wang, et al. (2022) "AAV2-mediated gene therapy for Bietti crystalline dystrophy provides functional CYP4V2 in multiple relevant cell models", Scientific Reports, 12: 9525, 13 pages long. (Year: 2022).*

Huang, et al. (2021) "Leber's Congenital Amaurosis: Current Concepts of Genotype-Phenotype Correlations", Genes, 12: 1261, 18 pages long. (Year: 2021).*

Seokmann, et al. (1999) "Immune Privilege: Keeping an Eye on Natural Killer T Cells", 190(9): 1197-1200. (Year: 1999).*

Tso, et al (1975) "Blood-Brain Barrier at the Optic Nerve Head?", Archives of Ophthalmology, 93: 815-25. (Year: 1975).*

Chaikitmongkol, V., et al. (2018). "Repeatability and Agreement of Visual Acuity Using the ETDRS Number Chart, Landolt C Chart, or ETDRS Alphabet Chart in Eyes With or Without Sight-Threatening Diseases." *JAMA Ophthalmol* 136(3): 286-290.

Chung, D. C., et al. (2018). "Novel mobility test to assess functional vision in patients with inherited retinal dystrophies." *Clin Exp Ophthalmol* 46(3): 247-259.

Zhong, X., Gutierrez, C., Xue, T et al,. Generation of three-dimensional retinal tissue with functional photoreceptors from human iPSCs. *Nat Commun* 5, 4047 (2014).

* cited by examiner

*Primary Examiner* — Robert M Kelly

(74) *Attorney, Agent, or Firm* — KNOBBE, MARTENS, OLSON & BEAR LLP

(57) ABSTRACT

The present application relates to a vector comprising a polynucleotide encoding CYP4V2 and a promoter operably linked to the polynucleotide encoding CYP4V2. The vector described herein has a good expression effect, high expression speed, and more stable expression intensity. The present application also provides cells, pharmaceutical compositions, and kits comprising the vector, and methods for treating, alleviating, and/or preventing a disease or disorder associated with retinal pigment epithelium (RPE) atrophy.

9 Claims, 16 Drawing Sheets

Specification includes a Sequence Listing.

ITR promoter hCYP4V2 polyA signal ITR
Fig. 1
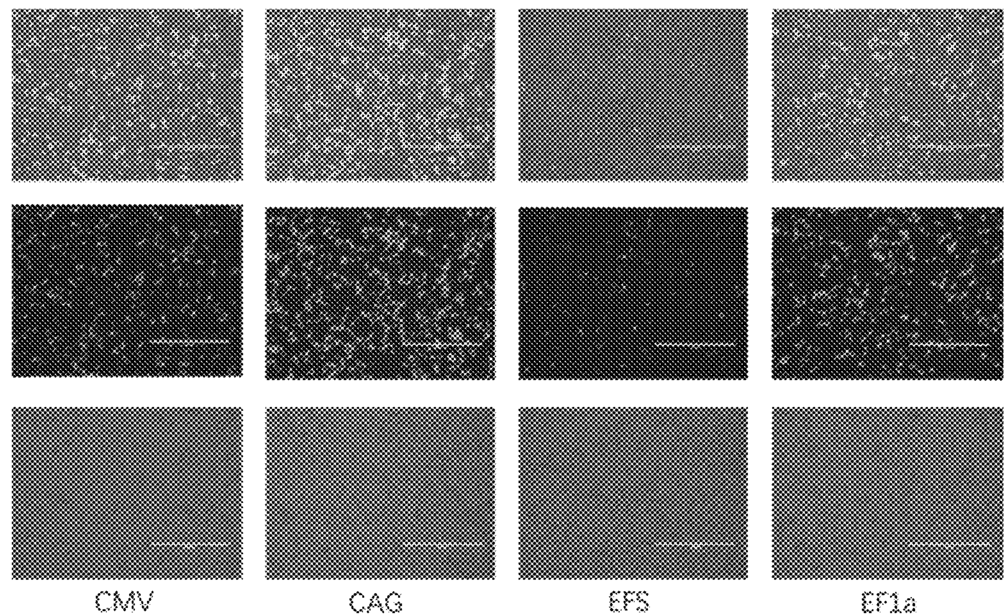
Fig. 2A
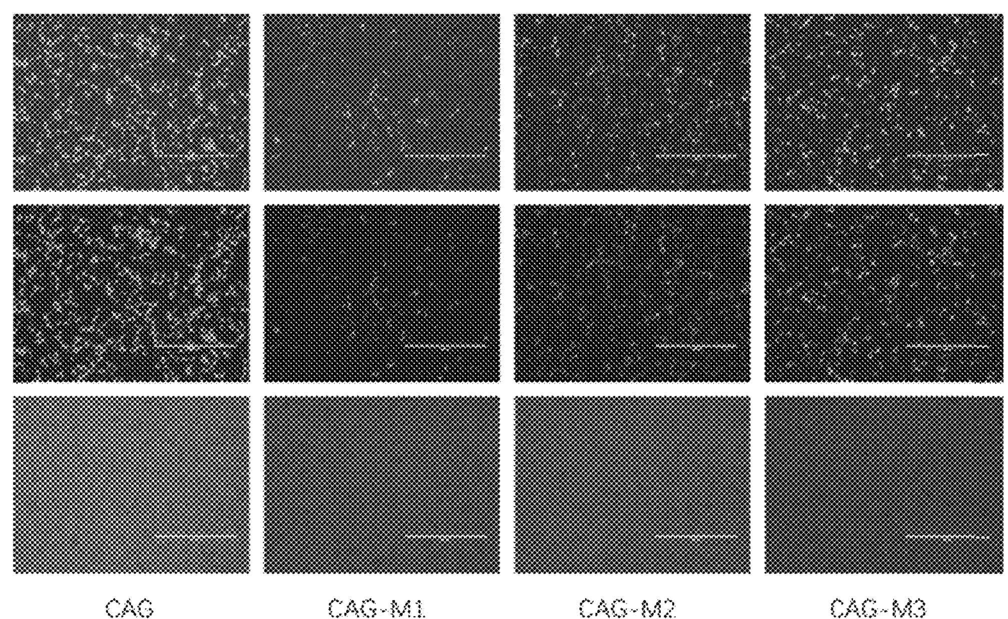
Fig. 2B

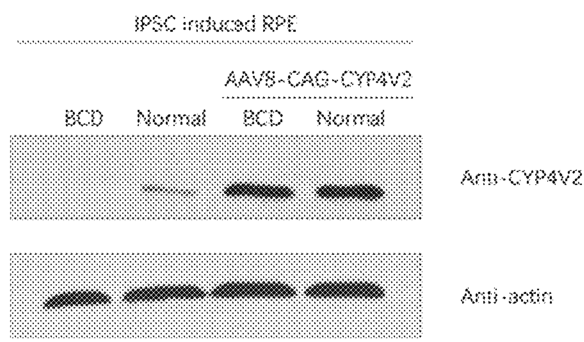
Fig. 12B
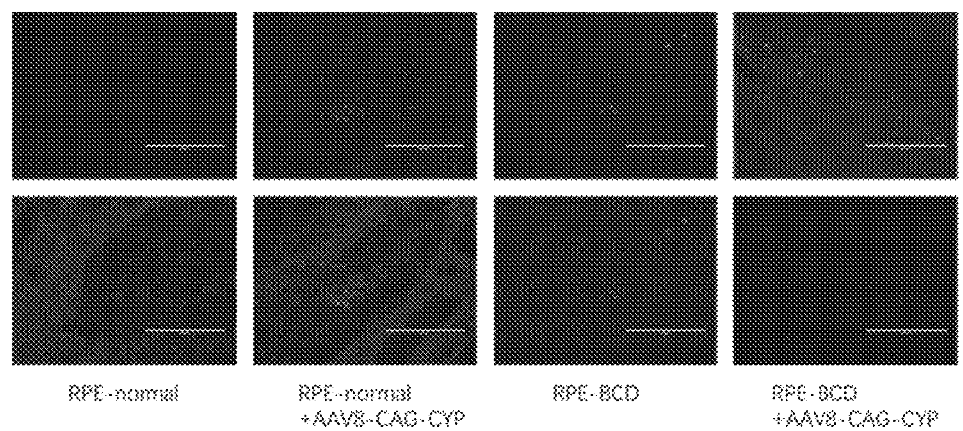
Fig. 13
Fig. 14A

SEQUENCE LISTING

```
Sequence total quantity: 23
SEQ ID NO: 1            moltype = DNA  length = 6202
FEATURE                 Location/Qualifiers
source                  1..6202
                        mol_type = other DNA
                        organism = synthetic construct
SEQUENCE: 1
cctgcaggca gctgcgcgct cgctcgctca ctgaggccgc ccgggcgtcg ggcgaccttt  60
ggtcgcccgg cctcagtgag cgagcgagcg cgcagagagg gagtggccaa ctccatcact  120
aggggttcct gcggccggtc gcgtctagta ctagtctagt cgcgtaccat tgacgtcaat  180
aatgacgtat gttcccatag taacgccaat agggactttc cattgacgtc aatgggtgga  240
gtatttacgg taaactgccc acttggcagt acatcaagtg tatcatatgc caagtacgcc  300
ccctattgac gtcaatgacg gtaaatggcc cgcctggcat tatgcccagt acatgacctt  360
atgggacttt cctacttggc agtacatcta cgtattagtc atcgctatta ccatggtcga  420
ggtgagcccc acgttctgct tcactctccc catctccccc ccctccccac ccccaatttt  480
gtatttattt atttttaat tattttgtgc agcgatgggg gcgggggggg ggggggggcg  540
cgcgccaggc ggggcggggc ggggcgaggg gcggggcggg gcgaggcgga gaggtgcggc  600
ggcagccaat cagagcggcg cgctccgaaa gtttcctttt atggcgaggc ggcggcggcg  660
gcggccctat aaaaagcgaa gcgcgcggcg ggcgggagtc gctgcgacgc tgccttcgcc  720
ccgtgccccg ctccgccgcc gcctcgcgcc gcccgccccg gctctgactg accgcgttac  780
tcccacaggt gagcgggcgg gacggccctt ctcctccggg ctgtaattag cgcttggttt  840
aatgacggct tgtttctttt ctgtggctgc gtgaaagcct tgaggggctc cgggagggcc  900
ctttgtgcgg ggggagcggc tcggggctgt ccgcgggggg acggctgcct tcgggggga  960
cggggcaggg cggggttcgg cttctggcgt gtgaccggcg gctctagagc ctctgctaac  1020
catgttcatg ccttcttctt tttcctacag ctcctgggca acgtgctggt tattgtgctg  1080
tctcatcatt ttggcaaaga attggatcgg taccgaggag atctgccacc atggcggggc  1140
tctggctggg gctcgtgtgg cagaagctgc tgctgtgggg cgcggcgagt gccctttccc  1200
tggccggcgc cagtctggtc ctgagcctgc tgcagagggt ggcgagctac gcgcggaaat  1260
ggcagcagat gcggcccatc cccacggtgg cccgcgccta cccactggtg ggccacgcgc  1320
tgctgatgaa gccggacggg cgagaatttt ttcagcagat cattgagtac acagaggaat  1380
accgccacat gccgctgctg aagctctggg tcgggccagt gcccatggtg gccctttata  1440
atgcagaaaa tgtggaggta attttaacta gttcaaagca aattgacaaa tcctctatgt  1500
acaagttttt agaaccatgg cttggcctag gacttcttac aagtactgga aacaaatggc  1560
gctccaggag aaagatgtta acacccactt tccattttac cattctggaa gatttcttag  1620
atatcatgaa tgaacaagca aatatattgg ttaagaaact tgaaaaacac attaaccaag  1680
aagcatttaa ctgctttttt tacatcactc tttgtgcctt agatatcatc tgtgaaacag  1740
ctatggggaa gaatattggt gctcaaagta atgatgattc cgagtatgtc cgtgcagttt  1800
atagaatgag tgagatgata tttcgaagaa taaagatgcc ctggctttgg cttgatctct  1860
ggtaccttat gtttaaagaa ggatgggaac acaaaaagag ccttcagatc ctacatactt  1920
ttaccaacag tgtcatcgct gaacgggcca atgaaatgaa cgccaatgaa gactgtagag  1980
gtgatggcag gggctctgcc ccctccaaaa ataaacgcag ggcctttctt gacttgcttt  2040
taagtgtgac tgatgacgaa gggaacaggc taagtcatga agatattcga gaagaagttg  2100
acaccttcat gtttgagggg cacgatacaa ctgcagctgc aataaactgg tccttatacc  2160
tgttgggttc taacccagaa gtccagaaaa aagtggatca tgaattggat gacgtgtttg  2220
ggaagtctga ccgtcccgct acagtagaag acctgaagaa acttcggtat ctggaatgtg  2280
ttattaagga gacccttcgc ctttttcctt ctgttccttt atttgcccgt agtgttagtg  2340
aagattgtga agtggcaggt tacagagttc taaaaggcac tgaagccgtc atcattccct  2400
atgcattgca cagagatccg agatacttcc ccaaccccga ggagttccag cctgagcggt  2460
tcttccccga gaatgcacaa gggcgccatc catatgccta cgtgcccttc tctgctggcc  2520
ccaggaactg tataggtcaa aagtttgctg tgatggaaga aaagaccatt ctttcgtgca  2580
tcctgaggca cttttggata gaatccaacc agaaaagaga agagcttggt ctagaaggac  2640
agttgattct tcgtccaagt aatggcatct ggatcaagtt gaagaggaga aatgcagatg  2700
aacgctaaac gcgtggttta tccgatccac cggatctaga taagatatcc gatccaccgg  2760
atctagataa ctgatcataa tcagccatac cacatttgta gaggttttac ttgctttaaa  2820
aaacctccca cacctccccc tgaacctgaa acataaaatg aatgcaattg gcggccgcct  2880
cgagctgtgc cttctagttg ccagccatct gttgtttgcc cctcccccgt gccttccttg  2940
accctggaag gtgccactcc cactgtcctt tcctaataaa atgaggaaat tgcatcgcat  3000
tgtctgagta ggtgtcattc tattctgggg ggtggggtgg ggcaggacag caagggggag  3060
gattgggaag acaatagcag gcatgctggg gatgcggtgg gctctatggg gtaaccacgt  3120
gcggacccaa cggccgcagg aacccctagt gatggagttg gccactccct ctctgcgcgc  3180
tcgctcgctc actgaggccg ggcgaccaaa ggtcgcccga cgcccgggct ttgcccgggc  3240
ggcctcagtg agcgagcgag cgcgcagctg cctgcagggg cgcctgatgc ggtattttct  3300
ccttacgcat ctgtgcggta tttcacaccg catacgtcaa agcaaccata gtacgcgccc  3360
tgtagcggca cattaagcgc ggcgggtgtg gtggttacgc gcagcgtgac cgctacactt  3420
gccagcgcct tagcgcccgc tcctttcgct ttcttccctt cctttctcgc cacgttcgcc  3480
```

```
ggctttcccc gtcaagctct aaatcggggg ctccctttag ggttccgatt tagtgcttta  3540
cggcacctcg accccaaaaa acttgatttg ggtgatggtt cacgtagtgg gccatcgccc  3600
tgatagacgg tttttcgccc tttgacgttg gagtccacgt tctttaatag tggactcttg  3660
ttccaaactg gaacaacact caactctatc tcgggctatt cttttgattt ataagggatt  3720
ttgccgattt cggtctattg gttaaaaaat gagctgattt aacaaaaatt taacgcgaat  3780
tttaacaaaa tattaacgtt tacaatttta tggtgcactc tcagtacaat ctgctctgat  3840
gccgcatagt taagccagcc ccgacacccg ccaacacccg ctgacgcgcc ctgacgggct  3900
tgtctgctcc cggcatccgc ttacagacaa gctgtgaccg tctccgggag ctgcatgtgt  3960
cagaggtttt caccgtcatc accgaaacgc gcgagacgaa agggcctcgt gatacgccta  4020
tttttatagg ttaatgtcat gataataatg gtttcttaga cgtcaggtgg cacttttcgg  4080
ggaaatgtgc gcggaacccc tatttgttta tttttctaaa tacattcaaa tatgtatccg  4140
ctcatgagac aataaccctg ataaatgctt caataatatt gaaaaaggaa gagtcctgag  4200
gcggaaagaa ccagctgtgg aatgtgtgtc agttagggtg tggaaagtcc ccaggctccc  4260
cagcaggcag aagtatgcaa agcatgcatc tcaattagtc agcaaccagg tgtggaaagt  4320
ccccaggctc cccagcaggc agaagtatgc aaagcatgca tctcaattag tcagcaacca  4380
tagtcccgcc cctaactccg cccatcccgc ccctaactcc gcccagttcc gcccattctc  4440
cgccccatgg ctgactaatt ttttttattt atgcagaggc cgaggccgcc tcggcctctg  4500
agctattcca gaagtagtga ggaggctttt ttggaggcct aggcttttgc aaagatcgat  4560
caagagacag gatgaggatc gtttcgcatg attgaacaag atggattgca cgcaggttct  4620
ccggccgctt gggtggagag gctattcggc tatgactggg cacaacagac aatcggctgc  4680
tctgatgccg ccgtgttccg gctgtcagcg caggggcgcc cggttctttt tgtcaagacc  4740
gacctgtccg gtgccctgaa tgaactgcaa gacgaggcag cgcggctatc gtggctggcc  4800
acgacgggcg ttccttgcgc agctgtgctc gacgttgtca ctgaagcggg aagggactgg  4860
ctgctattgg gcgaagtgcc ggggcaggat ctcctgtcat ctcaccttgc tcctgccgag  4920
aaagtatcca tcatggctga tgcaatgcgg cggctgcata cgcttgatcc ggctacctgc  4980
ccattcgacc accaagcgaa acatcgcatc gagcgagcac gtactcggat ggaagccggt  5040
cttgtcgatc aggatgatct ggacgaagag catcaggggc tcgcgccagc cgaactgttc  5100
gccaggctca aggcgagcat gcccgacggc gaggatctcg tcgtgaccca tggcgatgcc  5160
tgcttgccga atatcatggt ggaaaatggc cgcttttctg gattcatcga ctgtggccgg  5220
ctgggtgtgg cggaccgcta tcaggacata gcgttggcta cccgtgatat tgctgaagag  5280
cttggcggcg aatgggctga ccgcttcctc gtgctttacg gtatcgccgc tcccgattcg  5340
cagcgcatcg ccttctatcg ccttcttgac gagttcttct gactgtcaga ccaagtttac  5400
tcatatatac tttagattga tttaaaactt catttttaat ttaaaaggat ctaggtgaag  5460
atcctttttg ataatctcat gaccaaaatc ccttaacgtg agttttcgtt ccactgagcg  5520
tcagaccccg tagaaaagat caaaggatct tcttgagatc cttttttttct gcgcgtaatc  5580
tgctgcttgc aaacaaaaaa accaccgcta ccagcggtgg tttgtttgcc ggatcaagag  5640
ctaccaactc tttttccgaa ggtaactggc ttcagcagag cgcagatacc aaatactgtt  5700
cttctagtgt agccgtagtt aggccaccac ttcaagaact ctgtagcacc gcctacatac  5760
ctcgctctgc taatcctgtt accagtggct gctgccagtg gcgataagtc gtgtcttacc  5820
gggttggact caagacgata gttaccggat aaggcgcagc ggtcgggctg aacggggggt  5880
tcgtgcacac agcccagctt ggagcgaacg acctacaccg aactgagata cctacagcgt  5940
gagctatgag aaagcgccac gcttcccgaa gggagaaagg cggacaggta tccggtaagc  6000
ggcagggtcg gaacaggaga gcgcacgagg gagcttccag ggggaaacgc ctggtatctt  6060
tatagtcctg tcgggtttcg ccacctctga cttgagcgtc gatttttgtg atgctcgtca  6120
gggggcgga gcctatggaa aaacgccagc aacgcggcct ttttacggtt cctggccttt  6180
tgctggcctt ttgctcacat gt                                            6202
```

```
SEQ ID NO: 2            moltype = DNA  length = 937
FEATURE                 Location/Qualifiers
source                  1..937
                        mol_type = other DNA
                        organism = synthetic construct
SEQUENCE: 2
ccattgacgt caataatgac gtatgttccc atagtaacgc caatagggac tttccattga  60
cgtcaatggg tggagtattt acggtaaact gcccacttgg cagtacatca agtgtatcat  120
atgccaagta cgccccctat tgacgtcaat gacggtaaat ggcccgcctg gcattatgcc  180
cagtacatga ccttatggga ctttcctact tggcagtaca tctacgtatt agtcatcgct  240
attaccatgg tcgaggtgag ccccacgttc tgcttcactc tccccatctc ccccccctcc  300
ccacccccaa ttttgtattt atttattttt taattatttt gtgcagcgat gggggcgggg  360
gggggggggg ggcgcgcgcc aggcggggcg gggcggggcg aggggcgggg cggggcgagg  420
cggagaggtg cggcggcagc caatcagagc ggcgcgctcc gaaagtttcc ttttatggcg  480
aggcggcggc ggcggcggcc ctataaaaag cgaagcgcgc ggcgggcggg agtcgctgcg  540
acgctgcctt cgccccgtgc cccgctccgc cgccgcctcg cgccgcccgc cccggctctg  600
actgaccgcg ttactcccac aggtgagcgg gcgggacggc ccttctcctc cgggctgtaa  660
ttagcgcttg gtttaatgac ggcttgtttc ttttctgtgg ctgcgtgaaa gccttgaggg  720
gctccgggag ggccctttgt gcggggggag cggctcgggg ctgtccgcgg ggggacggct  780
gccttcgggg gggacggggc agggcggggt tcggcttctg gcgtgtgacc ggcggctcta  840
gagcctctgc taaccatgtt catgccttct tctttttcct acagctcctg ggcaacgtgc  900
tggttattgt gctgtctcat cattttggca aagaatt                            937
```

```
SEQ ID NO: 3            moltype = DNA  length = 225
FEATURE                 Location/Qualifiers
source                  1..225
                        mol_type = other DNA
                        organism = synthetic construct
SEQUENCE: 3
ctgtgccttc tagttgccag ccatctgttg tttgcccctc ccccgtgcct tccttgaccc  60
tggaaggtgc cactcccact gtcctttcct aataaaatga ggaaattgca tcgcattgtc  120
tgagtaggtg tcattctatt ctggggggtg gggtggggca ggacagcaag ggggaggatt  180
```

-continued

```
gggaagacaa tagcaggcat gctggggatg cggtgggctc tatgg                 225

SEQ ID NO: 4            moltype = DNA  length = 1578
FEATURE                 Location/Qualifiers
source                  1..1578
                        mol_type = genomic DNA
                        organism = Homo sapiens
SEQUENCE: 4
atggcggggc tctggctggg gctcgtgtgg cagaagctgc tgctgtgggg cgcggcgagt  60
gcccttccc tggccggcgc cagtctggtc ctgagcctgc tgcagagggt ggcgagctac   120
gcgcggaaat ggcagcagat gcggcccatc cccacggtgg cccgcgccta cccactggtg  180
ggccacgcgc tgctgatgaa gccggacggg cgagaatttt ttcagcagat cattgagtac  240
acagaggaat accgccacat gccgctgctg aagctctggg tcgggccagt gcccatggtg  300
gcccttata atgcagaaaa tgtggaggta attttaacta gttcaaagca aattgacaaa   360
tcctctatgt acaagttttt agaaccatgg cttggcctag gacttcttac aagtactgga  420
aacaaatggc gctccaggag aaagatgtta acacccactt tccattttac cattctggaa  480
gatttcttag atatcatgaa tgaacaagca aatatattgg ttaagaaact tgaaaaacac  540
attaaccaag aagcatttaa ctgctttttt tacatcactc tttgtgcctt agatatcatc  600
tgtgaaacag ctatggggaa gaatattggt gctcaaagta atgatgattc cgagtatgtc  660
cgtgcagttt atagaatgag tgagatgata tttcgaagaa taaagatgcc ctggctttgg  720
cttgatctct ggtaccttat gtttaaagaa ggatgggaac acaaaaagag ccttcagatc  780
ctacatactt ttaccaacag tgtcatcgct gaacgggcca atgaaatgaa cgccaatgaa  840
gactgtagag gtgatggcag gggctctgcc ccctccaaaa ataaacgcag ggcctttctt  900
gacttgcttt taagtgtgac tgatgacgaa gggaacaggc taagtcatga agatattcga  960
gaagaagttg acaccttcat gtttgagggg cacgatacaa ctgcagctgc aataaactgg  1020
tccttatacc tgttgggttc taacccagaa gtccagaaaa aagtggatca tgaattggat  1080
gacgtgtttg ggaagtctga ccgtcccgct acagtagaag acctgaagaa acttcggtat  1140
ctggaatgtg ttattaagga gacccttcgc ctttttcctt ctgttccttt atttgcccgt  1200
agtgttagtg aagattgtga agtggcaggt tacagagttc taaaaggcac tgaagccgtc  1260
atcattccct atgcattgca cagagatccg agatacttcc ccaaccccga ggagttccag  1320
cctgagcggt tcttccccga gaatgcacaa gggcgccatc catatgccta cgtgcccttc  1380
tctgctggcc ccaggaactg tataggtcaa aagtttgctg tgatggaaga aaagaccatt  1440
ctttcgtgca tcctgaggca cttttggata gaatccaacc agaaaagaga agagcttggt  1500
ctagaaggac agttgattct tcgtccaagt aatggcatct ggatcaagtt gaagaggaga  1560
aatgcagatg aacgctaa                                                 1578

SEQ ID NO: 5            moltype = AA  length = 525
FEATURE                 Location/Qualifiers
source                  1..525
                        mol_type = protein
                        organism = Homo sapiens
SEQUENCE: 5
MAGLWLGLVW QKLLLWGAAS ALSLAGASLV LSLLQRVASY ARKWQQMRPI PTVARAYPLV  60
GHALLMKPDG REFFQQIIEY TEEYRHMPLL KLWVGPVPMV ALYNAENVEV ILTSSKQIDK  120
SSMYKFLEPW LGLGLLTSTG NKWRSRRKML TPTFHFTILE DFLDIMNEQA NILVKKLEKH  180
INQEAFNCFF YITLCALDII CETAMGKNIG AQSNDDSEYV RAVYRMSEMI FRRIKMPWLW  240
LDLWYLMFKE GWEHKKSLQI LHTFTNSVIA ERANEMNANE DCRGDGRGSA PSKNKRRAFL  300
DLLLSVTDDE GNRLSHEDIR EEVDTFMFEG HDTTAAAINW SLYLLGSNPE VQKKVDHELD  360
DVFGKSDRPA TVEDLKKLRY LECVIKETLR LFPSVPLFAR SVSEDCEVAG YRVLKGTEAV  420
IIPYALHRDP RYFPNPEEFQ PERFFPENAQ GRHPYAYVPF SAGPRNCIGQ KFAVMEEKTI  480
LSCILRHFWI ESNQKREELG LEGQLILRPS NGIWIKLKRR NADER                 525

SEQ ID NO: 6            moltype = DNA  length = 27
FEATURE                 Location/Qualifiers
source                  1..27
                        mol_type = other DNA
                        organism = synthetic construct
SEQUENCE: 6
ggatcggtac cgaggagatc tgccacc                                     27

SEQ ID NO: 7            moltype = DNA  length = 176
FEATURE                 Location/Qualifiers
source                  1..176
                        mol_type = other DNA
                        organism = synthetic construct
SEQUENCE: 7
acgcgtggtt tatccgatcc accggatcta gataagatat ccgatccacc ggatctagat  60
aactgatcat aatcagccat accacatttg tagaggtttt acttgcttta aaaaacctcc  120
cacacctccc cctgaacctg aaacataaaa tgaatgcaat tggcggccgc ctcgag      176

SEQ ID NO: 8            moltype = DNA  length = 3259
FEATURE                 Location/Qualifiers
source                  1..3259
                        mol_type = other DNA
                        organism = synthetic construct
SEQUENCE: 8
ggtaaccacg tgcggaccca acggccgcag gaacccctag tgatggagtt ggccactccc  60
tctctgcgcg ctcgctcgct cactgaggcc gggcgaccaa aggtcgcccg acgcccgggc  120
tttgcccggg cggcctcagt gagcgagcga gcgcgcagct gcctgcaggg gcgcctgatg  180
```

-continued

```
cggtattttc tccttacgca tctgtgcggt atttcacacc gcatacgtca aagcaaccat  240
agtacgcgcc ctgtagcggc acattaagcg cggcgggtgt ggtggttacg cgcagcgtga  300
ccgctacact tgccagcgcc ttagcgcccg ctcctttcgc tttcttccct tcctttctcg  360
ccacgttcgc cggctttccc cgtcaagctc taaatcgggg gctcccttta gggttccgat  420
ttagtgcttt acggcacctc gaccccaaaa aacttgattt gggtgatggt tcacgtagtg  480
ggccatcgcc ctgatagacg gtttttcgcc ctttgacgtt ggagtccacg ttctttaata  540
gtggactctt gttccaaact ggaacaacac tcaactctat ctcgggctat tcttttgatt  600
tataagggat tttgccgatt tcggtctatt ggttaaaaaa tgagctgatt taacaaaaat  660
ttaacgcgaa ttttaacaaa atattaacgt ttacaatttt atggtgcact ctcagtacaa  720
tctgctctga tgccgcatag ttaagccagc cccgacaccc gccaacaccc gctgacgcgc  780
cctgacgggc ttgtctgctc ccggcatccg cttacagaca agctgtgacc gtctccggga  840
gctgcatgtg tcagaggttt tcaccgtcat caccgaaacg cgcgagacga aagggcctcg  900
tgatacgcct atttttatag gttaatgtca tgataataat ggtttcttag acgtcaggtg  960
gcacttttcg gggaaatgtg cgcggaaccc ctatttgttt atttttctaa atacattcaa  1020
atatgtatcc gctcatgaga caataaccct gataaatgct tcaataatat tgaaaaagga  1080
agagtcctga ggcggaaaga accagctgtg gaatgtgtgt cagttagggt gtggaaagtc  1140
cccaggctcc ccagcaggca gaagtatgca aagcatgcat ctcaattagt cagcaaccag  1200
gtgtggaaag tccccaggct ccccagcagg cagaagtatg caaagcatgc atctcaatta  1260
gtcagcaacc atagtcccgc ccctaactcc gcccatcccg cccctaactc cgcccagttc  1320
cgcccattct ccgccccatg gctgactaat tttttttatt tatgcagagg ccgaggccgc  1380
ctcggcctct gagctattcc agaagtagtg aggaggcttt tttggaggcc taggcttttg  1440
caaagatcga tcaagagaca ggatgaggat cgtttcgcat gattgaacaa gatggattgc  1500
acgcaggttc tccggccgct tgggtggaga ggctattcgg ctatgactgg gcacaacaga  1560
caatcggctg ctctgatgcc gccgtgttcc ggctgtcagc gcaggggcgc ccggttcttt  1620
ttgtcaagac cgacctgtcc ggtgccctga atgaactgca agacgaggca gcgcggctat  1680
cgtggctggc cacgacgggc gttccttgcg cagctgtgct cgacgttgtc actgaagcgg  1740
gaagggactg gctgctattg ggcgaagtgc cggggcagga tctcctgtca tctcaccttg  1800
ctcctgccga gaaagtatcc atcatggctg atgcaatgcg gcggctgcat acgcttgatc  1860
cggctacctg cccattcgac caccaagcga aacatcgcat cgagcgagca cgtactcgga  1920
tggaagccgg tcttgtcgat caggatgatc tggacgaaga gcatcagggg ctcgcgccag  1980
ccgaactgtt cgccaggctc aaggcgagca tgcccgacgg cgaggatctc gtcgtgaccc  2040
atggcgatgc ctgcttgccg aatatcatgg tggaaaatgg ccgcttttct ggattcatcg  2100
actgtggccg gctgggtgtg gcggaccgct atcaggacat agcgttggct acccgtgata  2160
ttgctgaaga gcttggcggc gaatgggctg accgcttcct cgtgctttac ggtatcgccg  2220
ctcccgattc gcagcgcatc gccttctatc gccttcttga cgagttcttc tgactgtcag  2280
accaagttta ctcatatata ctttagattg atttaaaact tcatttttaa tttaaaagga  2340
tctaggtgaa gatccttttt gataatctca tgaccaaaat cccttaacgt gagttttcgt  2400
tccactgagc gtcagacccc gtagaaaaga tcaaaggatc ttcttgagat cctttttttc  2460
tgcgcgtaat ctgctgcttg caaacaaaaa aaccaccgct accagcggtg gtttgtttgc  2520
cggatcaaga gctaccaact ctttttccga aggtaactgg cttcagcaga gcgcagatac  2580
caaatactgt tcttctagtg tagccgtagt taggccacca cttcaagaac tctgtagcac  2640
cgcctacata cctcgctctg ctaatcctgt taccagtggc tgctgccagt ggcgataagt  2700
cgtgtcttac cgggttggac tcaagacgat agttaccgga taaggcgcag cggtcgggct  2760
gaacgggggg ttcgtgcaca cagcccagct tggagcgaac gacctacacc gaactgagat  2820
acctacagcg tgagctatga gaaagcgcca cgcttcccga agggagaaag gcggacaggt  2880
atccggtaag cggcagggtc ggaacaggag agcgcacgag ggagcttcca gggggaaacg  2940
cctggtatct ttatagtcct gtcgggtttc gccacctctg acttgagcgt cgatttttgt  3000
gatgctcgtc aggggggcgg agcctatgga aaaacgccag caacgcggcc tttttacggt  3060
tcctggcctt ttgctggcct tttgctcaca tgtcctgcag gcagctgcgc gctcgctcgc  3120
tcactgaggc cgcccgggcg tcgggcgacc tttggtcgcc cggcctcagt gagcgagcga  3180
gcgcgcagag agggagtggc caactccatc actaggggtt cctgcggccg gtcgcgtcta  3240
gtactagtct agtcgcgta                                                3259

SEQ ID NO: 9           moltype = DNA  length = 7620
FEATURE                Location/Qualifiers
source                 1..7620
                       mol_type = other DNA
                       organism = synthetic construct
SEQUENCE: 9
atcgttaacg ccccgcgccg gccgctctag aactagtgga tcccccggaa gatcagaagt  60
tcctattccg aagttcctat tctctagaaa gtataggaac ttctgatctg cgcagccgcc  120
atgccggggt tttacgagat tgtgattaag gtccccagcg accttgacga gcatctgccc  180
ggcatttctg acagctttgt gaactgggtg gccgagaagg aatgggagtt gccgccagat  240
tctgacatgg atctgaatct gattgagcag gcacccctga ccgtggccga gaagctgcag  300
cgcgactttc tgacggaatg gcgccgtgtg agtaaggccc cggaggccct tttctttgtg  360
caatttgaga agggagagag ctacttccac atgcacgtgc tcgtggaaac caccggggtg  420
aaatccatgg ttttgggacg tttcctgagt cagattcgcg aaaaactgat tcagagaatt  480
taccgcggga tcgagccgac tttgccaaac tggttcgcgg tcacaaagac cagaaatggc  540
gccggaggcg ggaacaaggt ggtggatgag tgctacatcc ccaattactt gctccccaaa  600
acccagcctg agctccagtg ggcgtggact aatatggaac agtatttaag cgcctgtttg  660
aatctcacgg agcgtaaacg gttggtggcg cagcatctga cgcacgtgtc gcagacgcag  720
gagcagaaca aagagaatca gaatcccaat tctgatgcgc cggtgatcag atcaaaaact  780
tcagccaggt acatggagct ggtcgggtgg ctcgtggaca aggggattac ctcggagaag  840
cagtggatcc aggaggacca ggcctcatac atctccttca atgcggcctc caactcgcgg  900
tcccaaatca aggctgcctt ggacaatgcg ggaaagatta tgagcctgac taaaaccgcc  960
cccgactacc tggtgggcca gcagcccgtg gaggacattt ccagcaatcg gatttataaa  1020
attttggaac taaacgggta cgatccccaa tatgcggctt ccgtctttct gggatgggcc  1080
acgaaaaagt tcggcaagag gaacaccatc tggctgtttg ggcctgcaac taccgggaag  1140
accaacatcg cggaggccat agcccacact gtgcccttct acgggtgcgt aaactggacc  1200
```

-continued

```
aatgagaact ttcccttcaa cgactgtgtc gacaagatgg tgatctggtg ggaggagggg  1260
aagatgaccg ccaaggtcgt ggagtcggcc aaagccattc tcggaggaag caaggtgcgc  1320
gtggaccaga aatgcaagtc ctcggcccag atagacccga ctcccgtgat cgtcacctcc  1380
aacaccaaca tgtgcgccgt gattgacggg aactcaacga ccttcgaaca ccagcagccg  1440
ttgcaagacc ggatgttcaa atttgaactc acccgccgtc tggatcatga ctttgggaag  1500
gtcaccaagc aggaagtcaa agactttttc cggtgggcaa aggatcacgt ggttgaggtg  1560
gagcatgaat tctacgtcaa aaagggtgga gccaagaaaa gacccgcccc cagtgacgca  1620
gatataagtg agcccaaacg ggtgcgcgag tcagttgcgc agccatcgac gtcagacgcg  1680
gaagcttcga tcaactacgc agacaggtac caaaacaaat gttctcgtca cgtgggcatg  1740
aatctgatgc tgtttccctg cagacaatgc gagagaatga atcagaattc aaatatctgc  1800
ttcactcacg gacagaaaga ctgtttagag tgctttcccg tgtcagaatc tcaacccgtt  1860
tctgtcgtca aaaaggcgta tcagaaactg tgctacattc atcatatcat gggaaaggtg  1920
ccagacgctt gcactgcctg cgatctggtc aatgtggatt tggatgactg catctttgaa  1980
caataaatga tttaaatcag gtatggctgc cgatggttat cttccagatt ggctcgagga  2040
caacctctct gagggcattc gcgagtggtg ggcgctgaaa cctggagccc cgaagcccaa  2100
agccaaccag caaaagcagg acgacggccg gggtctggtg cttcctggct acaagtacct  2160
cggacccttc aacggactcg acaaggggga gcccgtcaac gcggcggacg cagcggccct  2220
cgagcacgac aaggcctacg accagcagct gcaggcgggt gacaatccgt acctgcggta  2280
taaccacgcc gacgccgagt ttcaggagcg tctgcaagaa gatacgtctt ttgggggcaa  2340
cctcgggcga gcagtcttcc aggccaagaa gcgggttctc gaacctctcg gtctggttga  2400
ggaaggcgct aagacggctc ctggaaagaa gagaccggta gagccatcac cccagcgttc  2460
tccagactcc tctacgggca tcggcaagaa aggccaacag cccgccagaa aaagactcaa  2520
ttttggtcag actggcgact cagagtcagt tccagaccct caacctctcg gagaacctcc  2580
agcagcgccc tctggtgtgg gacctaatac aatggctgca ggcggtggcg caccaatggc  2640
agacaataac gaaggcgccg acggagtggg tagttcctcg ggaaattggc attgcgattc  2700
cacatggctg ggcgacagag tcatcaccac cagcacccga acctgggccc tgcccaccta  2760
caacaaccac ctctacaagc aaatctccaa cgggacatcg ggaggagcca ccaacgacaa  2820
cacctacttc ggctacagca ccccctgggg gtattttgac tttaacagat tccactgcca  2880
cttttcacca cgtgactggc agcgactcat caacaacaac tggggattcc ggcccaagag  2940
actcagcttc aagctcttca acatccaggt caaggaggtc acgcagaatg aaggcaccaa  3000
gaccatcgcc aataacctca ccagcaccat ccaggtgttt acggactcgg agtaccagct  3060
gccgtacgtt ctcggctctg cccaccaggg ctgcctgcct ccgttcccgg cggacgtgtt  3120
catgattccc cagtacggct acctaacact caacaacggt agtcaggccg tgggacgctc  3180
ctccttctac tgcctggaat actttccttc gcagatgctg agaaccggca acaacttcca  3240
gtttacttac accttcgagg acgtgccttt ccacagcagc tacgcccaca gccagagctt  3300
ggaccggctg atgaatcctc tgattgacca gtacctgtac tacttgtctc ggactcaaac  3360
aacaggaggc acggcaaata cgcagactct gggcttcagc caaggtgggc ctaatacaat  3420
ggccaatcag gcaaagaact ggctgccagg accctgttac cgccaacaac gcgtctcaac  3480
gacaaccggg caaaacaaca atagcaactt tgcctggact gctgggacca aataccatct  3540
gaatggaaga aattcattgg ctaatcctgg catcgctatg gcaacacaca aagacgacga  3600
ggagcgtttt tttcccagta acgggatcct gatttttggc aaacaaaatg ctgccagaga  3660
caatgcggat tacagcgatg tcatgctcac cagcgaggaa gaaatcaaaa ccactaaccc  3720
tgtggctaca gaggaatacg gtatcgtggc agataacttg cagcagcaaa acacggctcc  3780
tcaaattgga actgtcaaca gccagggggc cttacccggt atggtctggc agaaccggga  3840
cgtgtacctg cagggtccca tctgggccaa gattcctcac acggacggca acttccaccc  3900
gtctccgctg atgggcggct ttggcctgaa acatcctccg cctcagatcc tgatcaagaa  3960
cacgcctgta cctgcggatc ctccgaccac cttcaaccag tcaaagctga actctttcat  4020
cacgcaatac agcaccggac aggtcagcgt ggaaattgaa tgggagctgc agaaggaaaa  4080
cagcaagcgc tggaaccccg agatccagta cacctccaac tactacaaat ctacaagtgt  4140
ggactttgct gttaatacag aaggcgtgta ctctgaaccc cgccccattg gcacccgtta  4200
cctcacccgt aatctgtaat tgcttgttaa tcaataaacc gtttaattcg tttcagttga  4260
actttggtct ctgcgtattt ctttcttatc tagtttccat ggctacgtag ataagtagca  4320
tggcgggtta atcattaact acagcccggg cgtttaaaca gcgggcggag gggtggagtc  4380
gtgacgtgaa ttacgtcata gggttaggga ggtcctgtat tagaggtcac gtgagtgttt  4440
tgcgacattt tgcgacacca tgtggtctcg ctgggggggg gggcccgagt gagcacgcag  4500
ggtctccatt ttgaagcggg aggtttgaac gagcgctggc gcgctcactg gccgtcgttt  4560
tacaacgtcg tgactgggaa aaccctggcg ttacccaact taatcgcctt gcagcacatc  4620
ccccttcgc cagctggcgt aatagcgaag aggcccgcac cgatcgccct tcccaacagt  4680
tgcgcagcct gaatggcgaa tggaaattgt aagcgttaat attttgttaa aattcgcgtt  4740
aaatttttgt taaatcagct cattttttta accaataggc cgaaatcggc aaaatccctt  4800
ataaatcaaa agaatagacc gagatagggt tgagtgttgt tccagtttgg aacaagagtc  4860
cactattaag aacgtggact ccaacgtcaa agggcgaaaa accgtctatc agggcgatgg  4920
cccactacgt gaaccatcac cctaatcaag ttttttgggg tcgaggtgcc gtaaagcact  4980
aaatcggaac cctaaaggga gcccccgatt tagagcttga cggggaaagc cggcgaacgt  5040
ggcgagaaag gaagggaaga aagcgaaagg agcgggcgct agggcgctgg caagtgtagc  5100
ggtcacgctg cgcgtaacca ccacacccgc cgcgcttaat gcgccgctac agggcgcgtc  5160
aggtggcact tttcggggaa atgtgcgcgg aacccctatt tgtttatttt tctaaataca  5220
ttcaaatatg tatccgctca tgagacaata accctgataa atgcttcaat aatattgaaa  5280
aaggaagagt cctgaggcgg aaagaaccag ctgtggaatg tgtgtcagtt agggtgtgga  5340
aagtccccag gctccccagc aggcagaagt atgcaaagca tgcatctcaa ttagtcagca  5400
accaggtgtg gaaagtcccc aggctcccca gcaggcagaa gtatgcaaag catgcatctc  5460
aattagtcag caaccatagt cccgccccta actccgccca tcccgcccct aactccgccc  5520
agttccgccc attctccgcc ccatggctga ctaatttttt ttatttatgc agaggccgag  5580
gccgcctcgg cctctgagct attccagaag tagtgaggag gcttttttgg aggcctaggc  5640
ttttgcaaag atcgatcaag agacaggatg aggatcgttt cgcatgattg aacaagatgg  5700
attgcacgca ggttctccgg ccgcttgggt ggagaggcta ttcggctatg actgggcaca  5760
acagacaatc ggctgctctg atgccgccgt gttccggctg tcagcgcagg ggcgcccggt  5820
tctttttgtc aagaccgacc tgtccggtgc cctgaatgaa ctgcaagacg aggcagcgcg  5880
gctatcgtgg ctggccacga cgggcgttcc ttgcgcagct gtgctcgacg ttgtcactga  5940
```

```
agcgggaagg gactggctgc tattgggcga agtgccgggg caggatctcc tgtcatctca  6000
ccttgctcct gccgagaaag tatccatcat ggctgatgca atgcggcggc tgcatacgct  6060
tgatccggct acctgcccat tcgaccacca agcgaaacat cgcatcgagc gagcacgtac  6120
tcggatggaa gccggtcttg tcgatcagga tgatctggac gaagagcatc aggggctcgc  6180
gccagccgaa ctgttcgcca ggctcaaggc gagcatgccc gacggcgagg atctcgtcgt  6240
gacccatggc gatgcctgct tgccgaatat catggtggaa aatggccgct tttctggatt  6300
catcgactgt ggccggctgg gtgtggcgga ccgctatcag gacatagcgt tggctacccg  6360
tgatattgct gaagagcttg gcggcgaatg ggctgaccgc ttcctcgtgc tttacggtat  6420
cgccgctccc gattcgcagc gcatcgcctt ctatcgcctt cttgacgagt tcttctgact  6480
gtcagaccaa gtttactcat atatacttta gattgattta aaacttcatt tttaatttaa  6540
aaggatctag gtgaagatcc tttttgataa tctcatgacc aaaatccctt aacgtgagtt  6600
ttcgttccac tgagcgtcag accccgtaga aaagatcaaa ggatcttctt gagatccttt  6660
ttttctgcgc gtaatctgct gcttgcaaac aaaaaaacca ccgctaccag cggtggtttg  6720
tttgccggat caagagctac caactctttt tccgaaggta actggcttca gcagagcgca  6780
gataccaaat actgttcttc tagtgtagcc gtagttaggc caccacttca agaactctgt  6840
agcaccgcct acatacctcg ctctgctaat cctgttacca gtggctgctg ccagtggcga  6900
taagtcgtgt cttaccgggt tggactcaag acgatagtta ccggataagg cgcagcggtc  6960
gggctgaacg gggggttcgt gcacacagcc cagcttggag cgaacgacct acaccgaact  7020
gagataccta cagcgtgagc tatgagaaag cgccacgctt cccgaaggga gaaaggcgga  7080
caggtatccg gtaagcggca gggtcggaac aggagagcgc acgagggagc ttccaggggg  7140
aaacgcctgg tatctttata gtcctgtcgg gtttcgccac ctctgacttg agcgtcgatt  7200
tttgtgatgc tcgtcagggg ggcggagcct atggaaaaac gccagcaacg cggccttttt  7260
acggttcctg gccttttgct ggccttttgc tcacatgttc tttcctgcgt tatcccctga  7320
ttctgtggat aaccgtatta ccgcctttga gtgagctgat accgctcgcc gcagccgaac  7380
gaccgagcgc agcgagtcag tgagcgagga agcggaagag cgcccaatac gcaaaccgcc  7440
tctccccgcg cgttggccga ttcattaatg cagctggcac gacaggtttc ccgactggaa  7500
agcgggcagt gagcgcaacg caattaatgt gagttagctc actcattagg caccccaggc  7560
tttacacttt atgcttccgg ctcgtatgtt gtgtggaatt gtgagcggat aacaatttca  7620

SEQ ID NO: 10          moltype =   length =
SEQUENCE: 10
000

SEQ ID NO: 11          moltype = DNA  length = 2943
FEATURE                Location/Qualifiers
source                 1..2943
                       mol_type = other DNA
                       organism = synthetic construct
SEQUENCE: 11
ccattgacgt caataatgac gtatgttccc atagtaacgc caatagggac tttccattga  60
cgtcaatggg tggagtattt acggtaaact gcccacttgg cagtacatca agtgtatcat  120
atgccaagta cgccccctat tgacgtcaat gacggtaaat ggcccgcctg gcattatgcc  180
cagtacatga ccttatggga ctttcctact tggcagtaca tctacgtatt agtcatcgct  240
attaccatgg tcgaggtgag ccccacgttc tgcttcactc tccccatctc ccccccctcc  300
ccacccccaa ttttgtattt atttattttt taattatttt gtgcagcgat gggggcgggg  360
gggggggggg ggcgcgcgcc aggcggggcg gggcggggcg aggggcgggg cggggcgagg  420
cggagaggtg cggcggcagc caatcagagc ggcgcgctcc gaaagtttcc ttttatggcg  480
aggcggcggc ggcggcggcc ctataaaaag cgaagcgcgc ggcgggcggg agtcgctgcg  540
acgctgcctt cgccccgtgc cccgctccgc cgccgcctcg cgccgcccgc cccggctctg  600
actgaccgcg ttactcccac aggtgagcgg gcgggacggc ccttctcctc cgggctgtaa  660
ttagcgcttg gtttaatgac ggcttgtttc ttttctgtgg ctgcgtgaaa gccttgaggg  720
gctccgggag ggccctttgt gcggggggag cggctcgggg ctgtccgcgg ggggacggct  780
gccttcgggg gggacggggc agggcggggt tcggcttctg gcgtgtgacc ggcggctcta  840
gagcctctgc taaccatgtt catgccttct tctttttcct acagctcctg ggcaacgtgc  900
tggttattgt gctgtctcat cattttggca aagaattgga tcggtaccga ggagatctgc  960
caccatggcg gggctctggc tggggctcgt gtggcagaag ctgctgctgt ggggcgcggc  1020
gagtgccctt tccctggccg gcgccagtct ggtcctgagc ctgctgcaga gggtggcgag  1080
ctacgcgcgg aaatggcagc agatgcggcc catccccacg gtggcccgcg cctacccact  1140
ggtgggccac gcgctgctga tgaagccgga cgggcgagaa ttttttcagc agatcattga  1200
gtacacagag gaataccgcc acatgccgct gctgaagctc tgggtcgggc cagtgcccat  1260
ggtggccctt tataatgcag aaaatgtgga ggtaatttta actagttcaa agcaaattga  1320
caaatcctct atgtacaagt ttttagaacc atggcttggc ctaggacttc ttacaagtac  1380
tggaaacaaa tggcgctcca ggagaaagat gttaacaccc actttccatt ttaccattct  1440
ggaagatttc ttagatatca tgaatgaaca agcaaatata ttggttaaga aacttgaaaa  1500
acacattaac caagaagcat ttaactgctt tttttacatc actctttgtg ccttagatat  1560
catctgtgaa acagctatgg ggaagaatat tggtgctcaa agtaatgatg attccgagta  1620
tgtccgtgca gtttatagaa tgagtgagat gatatttcga agaataaaga tgccctggct  1680
ttggcttgat ctctggtacc ttatgtttaa agaaggatgg gaacacaaaa agagccttca  1740
gatcctacat actttttacca acagtgtcat cgctgaacgg gccaatgaaa tgaacgccaa  1800
tgaagactgt agaggtgatg gcaggggctc tgccccctcc aaaaataaac gcagggcctt  1860
tcttgacttg cttttaagtg tgactgatga cgaagggaac aggctaagtc atgaagatat  1920
tcgagaagaa gttgacacct tcatgtttga ggggcacgat acaactgcag ctgcaataaa  1980
ctggtcctta tacctgttgg gttctaaccc agaagtccag aaaaaagtgg atcatgaatt  2040
ggatgacgtg tttgggaagt ctgaccgtcc cgctacagta gaagacctga agaaacttcg  2100
gtatctggaa tgtgttatta aggagaccct tcgccttttt ccttctgttc ctttatttgc  2160
ccgtagtgtt agtgaagatt gtgaagtggc aggttacaga gttctaaaag gcactgaagc  2220
cgtcatcatt ccctatgcat tgcacagaga tccgagatac ttccccaacc ccgaggagtt  2280
ccagcctgag cggttcttcc ccgagaatgc acaagggcgc catccatatg cctacgtgcc  2340
cttctctgct ggccccagga actgtatagg tcaaaagttt gctgtgatgg aagaaaagac  2400
```

```
cattctttcg tgcatcctga ggcacttttg gatagaatcc aaccagaaaa gagaagagct  2460
tggtctagaa ggacagttga ttcttcgtcc aagtaatggc atctggatca agttgaagag  2520
gagaaatgca gatgaacgct aaacgcgtgg tttatccgat ccaccggatc tagataagat  2580
atccgatcca ccggatctag ataactgatc ataatcagcc ataccacatt tgtagaggtt  2640
ttacttgctt taaaaaacct cccacacctc cccctgaacc tgaaacataa aatgaatgca  2700
attggcggcc gcctcgagct gtgccttcta gttgccagcc atctgttgtt tgcccctccc  2760
ccgtgccttc cttgaccctg gaaggtgcca ctcccactgt cctttcctaa taaaatgagg  2820
aaattgcatc gcattgtctg agtaggtgtc attctattct ggggggtggg gtggggcagg  2880
acagcaaggg ggaggattgg gaagacaata gcaggcatgc tggggatgcg gtgggctcta  2940
tgg                                                                2943

SEQ ID NO: 12          moltype = DNA  length = 122
FEATURE                Location/Qualifiers
source                 1..122
                       mol_type = genomic DNA
                       organism = Simian virus 40
SEQUENCE: 12
aacttgttta ttgcagctta taatggttac aaataaagca atagcatcac aaatttcaca  60
aataaagcat ttttttcact gcattctagt tgtggtttgt ccaaactcat caatgtatct  120
ta                                                                 122

SEQ ID NO: 13          moltype = DNA  length = 589
FEATURE                Location/Qualifiers
source                 1..589
                       mol_type = other DNA
                       organism = synthetic construct
SEQUENCE: 13
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgc              589

SEQ ID NO: 14          moltype = DNA  length = 717
FEATURE                Location/Qualifiers
source                 1..717
                       mol_type = other DNA
                       organism = synthetic construct
SEQUENCE: 14
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcg gtaacaactt  600
gtttattgca gcttataatg gttacaaata aagcaatagc atcacaaatt tcacaaataa  660
agcatttttt tcactgcatt ctagttgtgg tttgtccaaa ctcatcaatg tatctta    717

SEQ ID NO: 15          moltype = DNA  length = 820
FEATURE                Location/Qualifiers
source                 1..820
                       mol_type = other DNA
                       organism = synthetic construct
SEQUENCE: 15
aatcaacctc tggattacaa aatttgtgaa agattgactg gtattcttaa ctatgttgct  60
ccttttacgc tatgtggata cgctgcttta atgcctttgt atcatgctat tgcttcccgt  120
atggctttca ttttctcctc cttgtataaa tcctggttgc tgtctcttta tgaggagttg  180
tggcccgttg tcaggcaacg tggcgtggtg tgcactgtgt ttgctgacgc aacccccact  240
ggttggggca ttgccaccac ctgtcagctc ctttccggga ctttcgcttt ccccctccct  300
attgccacgg cggaactcat cgccgcctgc cttgcccgct gctggacagg ggctcggctg  360
ttgggcactg acaattccgt ggtgttgtcg gggaaatcat cgtcctttcc ttggctgctc  420
gcctgtgttg ccacctggat tctgcgcggg acgtccttct gctacgtccc ttcggccctc  480
aatccagcgg accttccttc ccgcggcctg ctgccggctc tgcggcctct tccgcgtctt  540
cgccttcgcc ctcagacgag tcggatctcc ctttgggccg cctccccgcc tcgagctgtg  600
ccttctagtt gccagccatc tgttgtttgc ccctcccccg tgccttcctt gaccctggaa  660
ggtgccactc ccactgtcct ttcctaataa aatgaggaaa ttgcatcgca ttgtctgagt  720
aggtgtcatt ctattctggg gggtggggtg gggcaggaca gcaaggggga ggattgggaa  780
gacaatagca ggcatgctgg ggatgcggtg ggctctatgg                        820

SEQ ID NO: 16          moltype = DNA  length = 584
```

-continued

```
FEATURE                Location/Qualifiers
source                 1..584
                       mol_type = genomic DNA
                       organism = cytomegalo virus
SEQUENCE: 16
gacattgatt attgactagt tattaatagt aatcaattac ggggtcatta gttcatagcc  60
catatatgga gttccgcgtt acataactta cggtaaatgg cccgcctggc tgaccgccca  120
acgacccccg cccattgacg tcaataatga cgtatgttcc catagtaacg ccaataggga  180
ctttccattg acgtcaatgg gtggagtatt tacggtaaac tgcccacttg gcagtacatc  240
aagtgtatca tatgccaagt acgcccccta ttgacgtcaa tgacggtaaa tggcccgcct  300
ggcattatgc ccagtacatg accttatggg actttcctac ttggcagtac atctacgtat  360
tagtcatcgc tattaccatg gtgatgcggt tttggcagta catcaatggg cgtggatagc  420
ggtttgactc acggggattt ccaagtctcc accccattga cgtcaatggg agtttgtttt  480
ggcaccaaaa tcaacgggac tttccaaaat gtcgtaacaa ctccgcccca ttgacgcaaa  540
tgggcggtag gcgtgtacgg tgggaggtct atataagcag agct                  584

SEQ ID NO: 17          moltype = DNA  length = 1163
FEATURE                Location/Qualifiers
source                 1..1163
                       mol_type = genomic DNA
                       organism = Homo sapiens
SEQUENCE: 17
gctccggtgc ccgtcagtgg gcagagcgca catcgcccac agtccccgag aagttggggg  60
gaggggtcgg caattgaacc ggtgcctaga gaaggtggcg cggggtaaac tgggaaagtg  120
atgtcgtgta ctggctccgc ctttttcccg agggtggggg agaaccgtat ataagtgcag  180
tagtcgccgt gaacgttctt tttcgcaacg ggtttgccgc cagaacacag gtaagtgccg  240
tgtgtggttc ccgcgggcct ggcctcttta cgggttatgg cccttgcgtg ccttgaatta  300
cttccacctg gctccagtac gtgattcttg atcccgagct ggagccaggg gcgggccttg  360
cgctttagga gccccttcgc ctcgtgcttg agttgaggcc tggcctgggc gctggggccg  420
ccgcgtgcga atctggtggc accttcgcgc ctgtctcgct gctttcgata agtctctagc  480
catttaaaat ttttgatgac ctgctgcgac gctttttttc tggcaagata gtcttgtaaa  540
tgcgggccag gatctgcaca ctggtatttc ggtttttggg cccgcggccg gcgacggggc  600
ccgtgcgtcc cagcgcacat gttcggcgag gcggggcctg cgagcgcggc caccgagaat  660
cggacggggg tagtctcaag ctggccggcc tgctctggtg cctggcctcg cgccgccgtg  720
tatcgccccg ccctgggcgg caaggctggc ccggtcggca ccagttgcgt gagcggaaag  780
atggccgctt cccggccctg ctccaggggg ctcaaaatgg aggacgcggc gctcgggaga  840
gcgggcgggt gagtcaccca cacaaaggaa aagggccttt ccgtcctcag ccgtcgcttc  900
atgtgactcc acggagtacc gggcgccgtc caggcacctc gattagttct ggagcttttg  960
gagtacgtcg tctttaggtt ggggggaggg gttttatgcg atggagtttc cccacactga  1020
gtgggtggag actgaagtta ggccagcttg gcacttgatg taattctcct tggaatttgg  1080
ccctttttgag tttggatctt ggttcattct caagcctcag acagtggttc aaagtttttt  1140
tcttccattt caggtgtcgt gag                                         1163

SEQ ID NO: 18          moltype = DNA  length = 212
FEATURE                Location/Qualifiers
source                 1..212
                       mol_type = genomic DNA
                       organism = Homo sapiens
SEQUENCE: 18
gggcagagcg cacatcgccc acagtccccg agaagttggg gggaggggtc ggcaattgaa  60
ccggtgccta gagaaggtgg cgcggggtaa actgggaaag tgatgtcgtg tactggctcc  120
gcctttttcc cgagggtggg ggagaaccgt atataagtgc agtagtcgcc gtgaacgttc  180
tttttcgcaa cgggtttgcc gccagaacac ag                               212

SEQ ID NO: 19          moltype = DNA  length = 687
FEATURE                Location/Qualifiers
source                 1..687
                       mol_type = other DNA
                       organism = synthetic construct
SEQUENCE: 19
tcgaggtgag ccccacgttc tgcttcactc tccccatctc ccccccctcc ccacccccaa  60
ttttgtattt atttattttt taattatttt gtgcagcgat gggggcgggg gggggggggg  120
ggcgcgcgcc aggcggggcg gggcggggcg aggggcgggg cggggcgagg cggagaggtg  180
cggcggcagc caatcagagc ggcgcgctcc gaaagtttcc ttttatggcg aggcggcggc  240
ggcggcggcc ctataaaaag cgaagcgcgc ggcgggcggg agtcgctgcg acgctgcctt  300
cgccccgtgc cccgctccgc cgccgcctcg cgccgcccgc cccggctctg actgaccgcg  360
ttactcccac aggtgagcgg gcgggacggc ccttctcctc cgggctgtaa ttagcgcttg  420
gtttaatgac ggcttgtttc ttttctgtgg ctgcgtgaaa gccttgaggg gctccgggag  480
ggccctttgt gcggggggag cggctcgggg ctgtccgcgg ggggacggct gccttcgggg  540
gggacggggc agggcggggt tcggcttctg gcgtgtgacc ggcggctcta gagcctctgc  600
taaccatgtt catgccttct tctttttcct acagctcctg ggcaacgtgc tggttattgt  660
gctgtctcat cattttggca aagaatt                                     687

SEQ ID NO: 20          moltype = DNA  length = 661
FEATURE                Location/Qualifiers
source                 1..661
                       mol_type = other DNA
                       organism = synthetic construct
SEQUENCE: 20
```

-continued

```
ccattgacgt caataatgac gtatgttccc atagtaacgc caatagggac tttccattga  60
cgtcaatggg tggagtattt acggtaaact gcccacttgg cagtacatca agtgtatcat  120
atgccaagta cgccccctat tgacgtcaat gacggtaaat ggcccgcctg gcattatgcc  180
cagtacatga ccttatggga ctttcctact tggcagtaca tctacgtatt agtcatcgct  240
attaccatgg tcgaggtgag ccccacgttc tgcttcactc tccccatctc ccccccctcc  300
ccacccccaa ttttgtattt atttattttt taattatttt gtgcagcgat gggggcgggg  360
gggggggggg ggcgcgcgcc aggcggggcg gggcggggcg aggggcgggg cggggcgagg  420
cggagaggtg cggcggcagc caatcagagc ggcgcgctcc gaaagtttcc ttttatggcg  480
aggcggcggc ggcggcggcc ctataaaaag cgaagcgcgc ggcgggcggt aagtatcaag  540
gttacaagac aggtttaagg agaccaatag aaactgggct tgtcgagaca gagaagactc  600
ttgcgtttct gataggcacc tattggtctt actgacatcc actttgcctt tctctccaca  660
g                                                                  661

SEQ ID NO: 21          moltype = DNA  length = 832
FEATURE                Location/Qualifiers
source                 1..832
                       mol_type = other DNA
                       organism = synthetic construct
SEQUENCE: 21
ggtgtggaaa gtccccaggc tccccagcag gcagaagtat gcaaagcatg catctcaatt  60
agtcagcaac caggtgtgga aagtccccag gctccccagc aggcagaagt atgcaaagca  120
tgcatctcaa ttagtcagca accatcgagg tgagccccac gttctgcttc actctcccca  180
tctccccccc ctccccaccc ccaattttgt atttatttat tttttaatta ttttgtgcag  240
cgatgggggc gggggggggg ggggggcgcg cgccaggcgg ggcggggcgg ggcgaggggc  300
ggggcggggc gaggcggaga ggtgcggcgg cagccaatca gagcggcgcg ctccgaaagt  360
ttccttttat ggcgaggcgg cggcggcggc ggccctataa aaagcgaagc gcgcggcggg  420
cgggagtcgc tgcgacgctg ccttcgcccc gtgccccgct ccgccgccgc ctcgcgccgc  480
ccgccccggc tctgactgac cgcgttactc ccacaggtga gcgggcggga cggcccttct  540
cctccgggct gtaattagcg cttggtttaa tgacggcttg tttcttttct gtggctgcgt  600
gaaagccttg aggggctccg ggagggccct ttgtgcgggg ggagcggctc ggggctgtcc  660
gcgggggggac ggctgccttc gggggggacg gggcagggcg ggttcggct tctggcgtgt  720
gaccggcggc tctagagcct ctgctaacca tgttcatgcc ttcttctttt tcctacagct  780
cctgggcaac gtgctggtta ttgtgctgtc tcatcatttt ggcaaagaat tg          832

SEQ ID NO: 22          moltype = DNA  length = 20
FEATURE                Location/Qualifiers
source                 1..20
                       mol_type = other DNA
                       organism = synthetic construct
SEQUENCE: 22
gcagatcatt gagtacacag                                              20

SEQ ID NO: 23          moltype = DNA  length = 20
FEATURE                Location/Qualifiers
source                 1..20
                       mol_type = other DNA
                       organism = synthetic construct
SEQUENCE: 23
ccgacccaga gcttcagcag                                              20
```

VECTOR AND METHOD FOR TREATING BIETTI'S CRYSTALLINE DYSTROPHY

TECHNICAL FIELD

The present application relates to the field of biomedicine, in particular to the vectors, related kits, and methods for treating Bietti's crystalline dystrophy (BCD).

BACKGROUND

Bietti's crystalline dystrophy (BCD) is a rare disease of retinal degeneration, and the symptoms mainly include crystals (transparent coverings) in the cornea; small, yellow or white, crystalline deposits deposited in the photosensitive tissues of the retina; and progressive atrophy of the retina, choriocapillary, and choroid. The deposits may damage the retina, causing gradual loss of vision. The deposits may cause damage to the retina, causing a gradual loss of vision.

Studies have shown that BCD is a genetic disease caused by CYP4V2 gene mutations, and it is generally believed that CYP4V2 gene mutations destroy its enzymatic function involved in fatty acid metabolism, thereby affecting the lipid decomposition. Although the study on CYP4V2 gene mutation provides the possibility for future gene therapy, there is no effective therapy at present.

SUMMARY

The present application provides a vector comprising a polynucleotide encoding CYP4V2 and a promoter operably linked to the polynucleotide encoding CYP4V2. The vector described herein has a good expression effect, a high expression speed, and a stable expression intensity. It can not only be expressed in RPE cells, but also can be effectively expressed in photoreceptor cell layer of retina. It has a wider expression range and can have a better therapeutic effect. The vector and/or the composition comprising the vector in the present application can effectively reduce the lipid deposition in RPE cells with CYP4V2 gene mutations; can restore the impaired fatty acid metabolism and normal function of lipid decomposition in BCD patients; can restore the phagocytosis by RPE cells in BCD patients and enhance the phagocytosis by normal human RPE cells; can significantly increase the amplitude in the electroretinogram of BCD mice and improve the retinal functions of BCD mice; and can improve the morphology of RPE cells in BCD mice and maintain RPE cell's number. The results of clinical trials show a remarkable visual functional gain in the BCD patients receiving the vector and/or the composition comprising the vector in the present application. In general, the present application provides a vector comprising a specific CYP4V2 gene sequence and a specific promoter sequence, which can significantly improve the expression of CYP4V2 protein, effectively improve the retinal function, and prevent or treat BCD. The vector described in the present application is effective and practical at different levels such as cell, organoid, and animal levels, as well as at human clinical level.

In one aspect, the present application provides a vector comprising a polynucleotide encoding CYP4V2 and a promoter operably linked to the polynucleotide encoding CYP4V2.

In some embodiments of the present invention, the promoter is a RPE cell-specific promoter, retinal cell-specific promoter, corneal cell-specific promoter, ocular cell-specific promoter, or constitutive promoter.

In some embodiments of the present invention, CYP4V2 has an amino acid sequence having at least 90%, at least 95%, at least 96%, at least 97%, at least 98%, at least 99%, or 100% identity to the amino acid sequence set forth in SEQ ID NO: 5, and/or the polynucleotide encoding CYP4V2 comprises a nucleotide sequence having at least 90%, at least 95%, at least 96%, at least 97%, at least 98%, at least 99%, or 100% identity to SEQ ID NO: 4, preferably CYP4V2 is mammalian CYP4V2.

In some embodiments of the present invention, the promoter is selected from CAG promoter (hybrid CMV early enhancer/chicken beta actin promoter, also known as CAGGS promoter, CB promoter, or CBA promoter), human beta actin promoter, small CBA (smCBA) promoter, CBS promoter or CBh promoter, elongation factor 1α short (EFS) promoter, elongation factor 1α (EF-1α) promoter, CMV promoter, PGK promoter, UBC promoter, GUSB promoter, UCOE promoter, VMD2 (also known as BEST1) promoter, OPEFS promoter, CYP4V2 native promoter, RPE65 promoter, or hybrids or derivatives thereof, preferably CAG promoter, more preferably the promoter comprises a nucleotide sequence set forth in any of SEQ ID NO: 2 or SEQ ID NOs: 19-21, most preferably comprises a nucleotide sequence set forth in SEQ ID NO: 2.

In some embodiments of the present invention, the vector is a viral vector, plasmid, or non-viral vector, preferably the viral vector is selected from retrovirus vector, adenovirus, adeno-associated virus (AAV) vector, herpesvirus vector, poxvirus vector, baculovirus vector, papillomavirus vector, papillomavirus (e.g., SV40) vector, more preferably recombinant AAV vector, wherein the serotype of the recombinant AAV vector is selected from: AAV1, AAV2, AAV3, AAV3B, AAV4, AAV5, AAV6, AAV7, AAV8, AAV9, AAV10, AAV11, AAV12, AAV13, AAV2/5, AAV2/8, AAV2/1, AAV2/9, AAV2/6, AAV2/4, AAV5/2, AAV8/1, AAV8/2, AAV2/7, AAV2/12, and AAV2/10, preferably AAV2 and AAV8, more preferably AAV2/8.

In some embodiments of the present invention, the vector further comprises a polyadenylation (PolyA) signal site located at 3' end of the polynucleotide encoding CYP4V2, preferably the polyadenylation (PolyA) signal site comprises a nucleotide sequence set forth in SEQ ID NO: 3; and/or the promoter is located at 5' end of the polynucleotide encoding CYP4V2.

In some embodiments of the present invention, the polynucleotide encoding CYP4V2 encodes the amino acid sequence set forth in SEQ ID NO: 5, the promoter comprises the nucleotide sequence set forth in SEQ ID NO: 2, and the vector is recombinant AAV2/8 vector.

In another aspect, the present invention provides a cell comprising the vector described herein.

In another aspect, the present invention provides a pharmaceutical composition comprising: a) the vector described herein; and b) a pharmaceutically acceptable adjuvant.

In some embodiments of the present invention, the adjuvant includes stabilizers, excipients, diluents, solubilizers, surfactants, emulsifiers, preservatives, or any combination thereof. Preferably, the adjuvant is suitable for subretinal administration.

In another aspect, the present invention provides a kit comprising: a) the vector or the pharmaceutical composition described herein; and b) helper plasmids or helper viruses that provide helper functions for virus packaging.

In another aspect, the present invention provides a method for treating, alleviating, and/or preventing a disease or disorder associated with retinal pigment epithelium (RPE)

atrophy, the method comprising administrating the vector according to the present invention to a subject in need thereof.

In some embodiments of the present invention, the disease or disorder includes Bietti's crystalline dystrophy.

In some embodiments of the present invention, the administration is subretinal injection.

In some embodiments of the present invention, the dosing volume is 50 μl-300 μl, and/or the dosage is $1\times10^{10}$ vg/eye-$1\times10^{12}$ vg/eye (vg, viral genome).

Other aspects and advantages of the present application can be readily appreciated by those skilled in the art from the detailed descriptions below. Only exemplary embodiments of the present application are shown and described in the detailed descriptions below. As will be recognized by those skilled in the art, the contents of the present application enable those skilled in the art to make changes to the specific embodiments without departing from the spirit and scope of the invention disclosed in the present application. Accordingly, the accompanying drawings and the descriptions in the specification of the present application are only exemplary and not restrictive.

DESCRIPTION OF THE DRAWINGS

The specific features of the invention disclosed in the present application are set forth in the appended claims. The characteristics and advantages of the invention disclosed in the present application can be better understood by reference to the exemplary embodiments described in detail below and the accompanying drawings. Brief descriptions of the accompanying drawings are as follows:

FIG. 1 shows a schematic diagram of the structure of the nucleic acid molecule described in the present application.

FIG. 2A and FIG. 2B show the GFP fluorescence intensities of vectors with different promoters.

FIG. 6A to FIG. 6E show the expressions of different serotypes of AAVs using the CMV promoter in mouse retina at 1 week after injection, wherein: FIG. 6A: AAV2; FIG. 6B: AAV5; FIG. 6C and FIG. 6D: AAV8; FIG. 6E: AAV9.

FIG. 10A: after 2 weeks; FIG. 10B: after 6 weeks.

FIG. 12B shows the CYP4V2 expression after infecting iPSC-induced RPE cells from healthy donors or BCD patients with AAV8-CAG-CYP4V2.

FIG. 13 shows the cell phagocytosis after infecting iPSC-induced RPE cells from healthy donors or BCD patients with AAV8-CAG-CYP4V2.

FIG. 14A shows a photograph of the subretinal injection in mice under a microscope.

DESCRIPTION OF EMBODIMENTS

Figure 3:
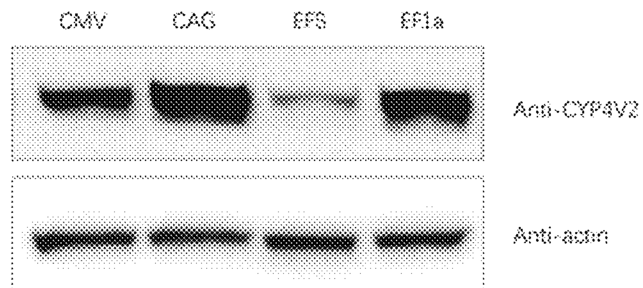
FIG. 3 shows the CYP4V2 protein expressions of vectors with different promoters.

The embodiments of the invention in the present application are described below by certain specific examples, and those skilled in the art can easily understand other advantages and effects of the invention in the present application from the contents disclosed in this specification.

Definitions of Terms

The present application is further described below: in the present invention, unless otherwise specified, the scientific and technical terms used herein have the meanings commonly understood by those skilled in the art. Moreover, the related terms and laboratory procedures in protein and nucleic acid chemistry, molecular biology, cell and tissue culture, microbiology, and immunology as used herein are the terms and routine procedures widely used in the corresponding fields. Meanwhile, for a better understanding of the present invention, the definitions and explanations of related terms are provided below.

As used herein, the term "CYP4V2" generally refers to a protein that is member 2 of subfamily V of cytochrome P450 family 4. The term "cytochrome P450," also known as CYP450, usually refers to a family of ferroheme proteins, belonging to a class of monooxygenases, and involved in the metabolism of endogenous substances or exogenous substances comprising drugs and environmental compounds. According to the identity degree of amino acid sequence, the members are divided into three levels: family, subfamily, and individual enzymes. The cytochrome P450 enzyme system may be abbreviated as CYP, wherein the family is represented by Arabic number, the subfamily is represented by English capital letter, and the individual enzyme is represented by Arabic number, such as CYP4V2 herein. The human CYP4V2 gene (HGNC: 23198), located at 4q35, has a full length of 19.28 kb with 11 exons, and plays an important role in fatty acid metabolism (Kumar S., Bioinformation, 2011, 7:360-365). CYP4V2 is expressed almost in all tissues, but is expressed at a higher level in the retina and retinal pigment epithelium while at a slightly lower level in the cornea tissues. The mutations in the CYP4V2 gene may be associated with Bietti's crystalline dystrophy and/or posterior retinitis pigmentosa.

As used herein, the term "polyadenylation (PolyA) sequence", also known as polyadenylation tail and PolyA tail, generally refers to a stretch of tens to hundreds of single adenosines added at 3' end of mRNA after transcription. The polyadenylation usually occurs during and after the transcription of deoxyribonucleic acid (DNA) into ribonucleic acid (RNA) in the nucleus, and this reaction is usually completed by PolyA polymerase. In the eukaryote, the polyadenylation is a mechanism by which the mRNA molecule is interrupted at its 3' end, and the PolyA sequence can protect mRNA from the attack of exonuclease, and is very important for the nuclear export, translation and stability of mRNA.

As used herein, the term "polyadenylation (PolyA) signal site" generally refers to a base sequence located at 3' end of messenger RNA (mRNA) that can be recognized by the polyadenylation-related cleavage factor. Usually, it is also a cis-regulatory signal on the mRNA. In general, the process of tailing (i.e., polyadenylation) begins after the termination of transcription, and tens to hundreds of single adenosines are added following 3' UTR in mRNA by the polyadenylation-related cleavage factor under the regulation of the PolyA signal site. The common tailing signals include SV40, BGH, HSV, TK signals, and the like. The polyadenylation-related cleavage factors may include cleavage/polyadenylation specific factor (CPSF), cleavage stimulation factor (CstF), cleavage factor I (CFI), cleavage factor II (CFII). The PolyA signal site may usually comprise an AAUAAA sequence, but it varies among eukaryotic groups. For example, most human PolyA signal sites comprise an AAUAAA sequence, but this sequence is less common in plants and fungi.

As used herein, the term "operably linked" generally refers to placing the regulatory sequence necessary for the expression of a coding sequence at an appropriate position relative to the coding sequence so as to effect the expression of the coding sequence. For example, when a first nucleic acid sequence is in a functional relationship with a second nucleic acid sequence, the first nucleic acid sequence is operably linked to the second nucleic acid sequence. In certain embodiments, the arrangement of coding sequences and transcription control elements in an expression vector can be represented. The control element may include promoter, enhancer, and termination element. For example, if a promoter influences the transcription or expression of a coding sequence, the promoter is operably linked to the coding sequence. In certain embodiments, "operably linked" can also refer to the ligation of a target gene into a vector such that transcription and translation control sequences within the vector exert their intended functions of regulating the transcription and translation of the target gene.

As used herein, the term "promoter" generally refers to a deoxyribonucleic acid (DNA) sequence that enables the transcription of a particular gene. The promoter can be recognized by RNA polymerase, and initiate the transcription and synthesis of RNA. During the synthesis of ribonucleic acid (RNA), the promoter can interact with the transcription factor for regulating the gene transcription, to control the initiation time and expression degree of the gene expression (transcription). The promoter comprises the core promoter region and the regulatory region, and is located in the regulatory sequence that controls the gene expression and upstream of the gene transcription initiation site (5' direction of the DNA antisense strand), and itself has no compilation function. According to the mode of action and function, the promoter is divided into three categories: constitutive promoter (consistent activity in most or all tissues), specific promoter (tissue specificity or specific for developmental stage), and inducible promoter (regulated by external chemical or physical signal).

As used herein, the term "retinal pigment epithelium (RPE)" generally refers to a layer of pigment cells immediately outside the retinal sensory nerves. The retinal pigment epithelium consists of a single layer of hexagonal cells that contain dense pigment granules. The retinal pigment epithelium (RPE) is closely connected with the underlying choroid and the upper retinal nerve cells. Its main functions may include: controlling the fluids and nutrition in the subretinal space; functioning as a blood-retinal barrier; synthesis of the growth factor for adjusting the local structure; absorption of lights and regulation of the electrical balance; regeneration and synthesis of visual pigments; phagocytosis and digestion of photoreceptor outer segments; maintenance of retinal attachment; and regeneration and repair after injury. RPE is generally considered to be an important tissue for maintaining the photoreceptor function, and is also affected by many lesions in the choroid and retina.

As used herein, the term "retinal pigment epithelium (RPE) atrophy" generally refers to degenerative changes in the retinal pigment epithelium (RPE) manifested by cell death or dysfunction. The age-related macular degeneration or retinitis pigmentosa (RP) is often accompanied by the retinal pigment epithelium atrophy. The retinitis pigmentosa (abbreviated as RP), also known as the retinal pigment lesion, usually refers to a class of inherited ocular diseases. There are three modes of inheritance: autosomal recessive, dominant, and X-linked recessive, and dihybrid inheritance and mitochondrial inheritance are also present. The common symptoms in the early stage may be night blindness, narrowing of visual field, the ability to see the scene right ahead but the inability to see the visual field slightly to the left and right, and then the gradual disappearance of vision. RP may include uniocular primary retinitis pigmentosa, sector primary retinitis pigmentosa, central or paracentral primary retinitis pigmentosa, retinitis pigmentosa sine pigmento, albescent punctate degeneration of retina, Bietti's crystalline dystrophy, pigmented paravenous retinitis pigmentosa, preserved para-arteriolar retinal pigment epithelium retinitis pigmentosa, Leber congenital amaurosis, and retinitis pigmentosa in other syndromes.

As used herein, the term "Bietti's crystalline dystrophy (BCD)" generally refers to a class of autosomal recessive ocular diseases first described in 1937 by an Italian ophthalmologist, Dr. GB Bietti. The symptoms mainly include crystals (transparent coverings) in the cornea; small, yellow or white, crystalline deposits deposited in the photosensitive tissues of the retina; and progressive atrophy of the retina, choriocapillary, and choroid. The Bietti's crystalline dystrophy may include a disease caused by CYP4V2 gene mutation.

As used herein, the term "vector" generally refers to a nucleic acid delivery vehicle into which a polynucleotide encoding a protein can be inserted to express the protein. Through the transformation, transduction, or transfection of a host cell with the vector, the genetic elements carried by the vector are expressed in the host cell. For example, the vector comprises: plasmid; phagemid; cosmid; artificial chromosome, such as yeast artificial chromosome (YAC), bacterial artificial chromosome (BAC), or P1-derived artificial chromosome (PAC); phage, such as k phage or M13 phage; viral vector; and the like. A vector may contain a variety of elements controlling expressions, comprising promoter sequence, transcription initiation sequence, enhancer sequence, selection element, and reporter gene. Additionally, the vector may also contain a replication origin. The vector may also comprise a component contributing to the entry into a cell, such as viral particle, liposome, or protein coat, but not limited to these substances.

As used herein, the term "viral vector" generally refers to a non-wild-type recombinant viral particle serving as a gene delivery vehicle and containing a recombinant viral genome packaged inside a viral capsid. The animal virus species used as the vector may include retrovirus (including lentivirus), adenovirus, adeno-associated virus (AAV), herpesvirus (such as herpes simplex virus), poxvirus, baculovirus, papillomavirus, and papovavirus (such as SV40).

As used herein, the term "AAV" is the standard abbreviation for adeno-associated virus. The adeno-associated virus is a single-stranded DNA parvovirus that grows only in cells, some functions of which are provided by the co-infection of helper virus. There are currently thirteen AAV serotypes that have been characterized, as shown in Table 1 below. General information and reviews on AAV can be found, for example, in Carter, 1989, Handbook of Parvoviruses, Vol. 1, pp. 169-228, and Berns, 1990, Virology, pp. 1743-1764, Raven Press, (New York). However, it is fully expected that these identical principles will apply to additional AAV serotypes, since the various serotypes are known to be very closely related, both structurally and functionally, even at the genetic level. For example, all AAV serotypes apparently exhibit very similar replication properties mediated by homologous rep genes; and all carry three related capsid proteins, such as those expressed in AAV6. The degree of correlation is further demonstrated by heteroduplex analysis, revealing the extensive cross-hybridization between serotypes along the length of the genome; as well as the presence of similar self-annealing segments at the end of inverted terminal repeat (ITR). Similar infection patterns also suggest that the replication functions in each serotype are under similar regulatory control.

TABLE 1

| AAV capsid protein serotype | |
|---|---|
| AAV serotype | NCBI GenBank accession number |
| AAV1 | NC_002077.1 |
| AAV2 | NC_001401.2 |
| AAV3 | NC_001729.1 |
| AAV3B | AF028705.1 |
| AAV4 | NC_001829.1 |
| AAV5 | NC_006152.1 |
| AAV6 | AF028704.1 |
| AAV7 | NC_006260.1 |
| AAV8 | NC_006261.1 |
| AAV9 | AX753250.1 |
| AAV10 | AY631965.1 |
| AAV11 | AY631966.1 |
| AAV12 | DQ813647.1 |
| AAV13 | EU285562.1 |

As used herein, the term "AAV vector" generally refers to a vector comprising one or more polynucleotides (or transgenes) of interest flanked by AAV inverted terminal repeats (ITRs). Such AAV vectors can be replicated and packaged into infectious virus particles when present in host cells that have been transfected with vectors encoding and expressing the rep and cap gene products. The term "AAV virion" or "AAV virus particle" or "AAV vector particle" refers to a virus particle composed of at least one AAV capsid protein and an encapsidated polynucleotide AAV vector. If the particle contains a heterologous polynucleotide (i.e., a polynucleotide other than the wild-type AAV genome, such as a transgene to be delivered into mammalian cells), it is often referred to as an "AAV vector particle" or simply referred to as "AAV vector." Thus, the production of AAV vector particles necessarily includes the production of AAV vectors such that the vectors are contained within the AAV vector particles.

The AAV "rep" gene and "cap" gene refer to the genes encoding the replication protein and capsid protein, respectively. The AAV rep and cap genes have been found in all AAV serotypes studied to date and are described herein and in the references cited. In the wild-type AAV, the rep and cap genes are generally adjacent to each other in the virus genome (i.e., they are "coupled" together into contiguous or overlapping transcriptional units), and they are generally conserved across AAV serotypes. The AAV rep and cap genes may also be referred to individually or collectively as "AAV packaging genes." The AAV cap gene encodes a Cap protein capable of packaging the AAV vector in the presence of rep and adenovirus helper functions and capable of binding to target cell receptors. In certain instances, the AAV cap gene encodes a capsid protein derived from a particular AAV serotype, such as those shown in Table 1.

The different serotypes of AAV have genomic sequences that are significantly homologous at the amino acid and nucleic acid levels, provide a set of similar genetic functions, produce virions that substantially are physically and functionally equivalent, and are replicated and assembled through nearly identical mechanisms.

The terms "polynucleotide," "nucleic acid molecule," "nucleotide sequence," "nucleic acid," and "oligonucleotide" are used interchangeably, and generally refer to a polymeric form of nucleotides (such as deoxyribonucleotides or ribonucleotides) of any length, or analogs thereof. The polynucleotide can have any three-dimensional structure and can perform any known or unknown function. The non-limiting examples of nucleic acid molecules are as follows: coding or non-coding region of gene or gene fragment, multiple loci (one locus) defined by ligation analysis, exon, intron, messenger RNA (mRNA), transporter RNA, ribosomal RNA, short interfering RNA (siRNA), short hairpin RNA (shRNA), micro-RNA (miRNA), ribozyme, cDNA, recombinant polynucleotide, branched polynucleotide, plasmid, vector, isolated DNA of any sequence, isolated RNA of any sequence, nucleic acid probe, and primer. The nucleic acid may contain one or more modified nucleotides, such as methylated nucleotides and nucleotide analogs. If present, the modification of nucleotide structure can be performed before or after polymer assembly. The sequence of nucleic acid molecule can be interrupted by a non-nucleotide component. The nucleic acid molecule can be further modified after polymerization, such as by conjugation to a labeling component.

As used herein, the terms "polypeptide," "peptide," and "protein" are used interchangeably, and generally refer to a polymer of amino acids of any length. The polymer may be linear or branched, and it may contain modified amino acids, and may be interrupted by non-amino acids. These terms also encompass amino acid polymers that have been modified. These modifications may include: disulfide bond formation, glycosylation, lipidation, acetylation, phosphorylation, or any other manipulation (e.g., binding to a labeling component).The term "amino acid" includes natural and/or non-natural or synthetic amino acids, including glycine and D and L optical isomers, as well as amino acid analogs and peptidomimetics.

In addition to the specific proteins and nucleic acid molecules mentioned herein, the present application may also include functional variants, derivatives, analogs, homologues, and fragments thereof.

The term "functional variant" refers to a polypeptide having substantially the same amino acid sequence or encoded by substantially the same nucleotide sequence as the naturally occurring sequence and capable of possessing one or more activities of the naturally occurring sequence. In the context of this application, a variant of any given sequence refers to a sequence in which a particular sequence of residues (whether amino acid or nucleotide residues) has been modified such that the polypeptide or polynucleotide substantially retains at least one endogenous functions. Variant sequences can be obtained by addition, deletion, substitution, modification, replacement, and/or variation of at least one amino acid residues and/or nucleotide residues present in a naturally occurring protein and/or polynucleotide, as long as the original functional activity is retained.

As used herein, the term "derivative" generally refers to the polypeptide or polynucleotide of the present application including any substitution, variation, modification, replacement, deletion, and/or addition of one amino acid residue (or multiple amino acid residues) of the sequence, as long as the resulting polypeptide or polynucleotide substantially retains at least one endogenous functions.

As used herein, the term "analog" generally refers to a polypeptide or polynucleotide that includes any mimetic of the polypeptide or polynucleotide, i.e., a chemical compound possessing at least one endogenous function of the polypeptide or polynucleotide which the mimetic mimics.

Generally, the amino acid substitutions, such as at least 1 (e.g., 1, 2, 3, 4, 5, 6, 7, 8, 9, 10, or more) amino acid substitutions, can be made, so long as the modified sequence substantially retains the desired activity or ability. The amino acid substitutions can include the use of non-naturally occurring analogs.

The proteins or polypeptides used herein may also have deletions, insertions, or substitutions of amino acid residues that produce silent changes and result in functionally equivalent proteins. The deliberate amino acid substitutions can be made based on the similarity in polarity, charge, solubility, hydrophobicity, hydrophilicity, and/or amphiphilic nature of the residues, so long as the endogenous function is retained. For example, negatively charged amino acids include aspartic acid and glutamic acid; positively charged amino acids include lysine and arginine; and amino acids containing uncharged polar headgroups with similar hydrophilicity values include asparagine, glutamine, serine, threonine, and tyrosine.

As used herein, the term "homologue" generally refers to an amino acid sequence or nucleotide sequence having a certain homology to a wild-type amino acid sequence and a wild-type nucleotide sequence. The term "homology" can be equivalent to the sequence "identity." A homologous sequence can include an amino acid sequence that is at least 80%, 85%, 90%, 99.1%, 99.2%, 99.3%, 99.4%, 99.5%, 99.6%, 99.7%, 99.8%, or 99.9% identical to the subject sequence. Typically, a homologue will contain the same active site as the subject amino acid sequence and the like. The homology can be considered in terms of similarity (i.e., amino acid residues with similar chemical properties/functions), or it can be expressed in terms of sequence identity. As used herein, a sequence having a percent identity to any of SEQ ID NOs of an amino acid sequence or a nucleotide sequence as mentioned refers to a sequence having said percent identity over the entire length of SEQ ID NO as mentioned.

To determine the sequence identity, the sequence alignment can be performed, which can be performed by various means known to those skilled in the art, for example using BLAST, BLAST-2, ALIGN, NEEDLE, or Megalign (DNASTAR) software, and the like. Those skilled in the art can determine the appropriate parameters for alignment, including any algorithm required to achieve optimal alignment among the full-length sequences to be compared.

As used herein, the term "preventing" generally refers to the prophylactic administration to a healthy subject to prevent the occurrence of a certain disease or disorder. It may also include the prophylactic administration of the agent to a patient in the early stage of an allergic disease to be treated. The term "preventing" does not require 100% elimination of the likelihood of a disease or disorder; in other words, the term "preventing" generally means that the likelihood of a disease or disorder is reduced in the presence of the administration.

As used herein, the term "alleviating" refers to reducing, diminishing, or retarding a certain condition, disease, disorder, or phenotype. The condition, disease, disorder, or phenotype may include subjective perceptions of the subject such as pain, dizziness, or other physiological disturbances, or focus conditions detected by medical laboratory means.

As used herein, the term "treating" generally refers to a clinical intervention for altering the natural course of the treated individual or cell in a clinical pathological process. It may include improving the disease status, eliminating lesions, or improving the prognosis.

As used herein, the term "cell" can generally be or has been a single cell, cell line or cell culture of a recipient for the nucleic acid molecule or vector. The cell may comprise the nucleic acid molecule described herein or the vector described herein. The cell may include the progeny of a single cell. Due to the natural, accidental, or intentional mutation, the progeny may not necessarily be completely identical to the original parent cell (either morphologically in total DNA complement, or genomically). The cell may include a cell transfected in vitro with the vector described herein. The cell may be bacterial cell (e.g., *E. coli*), yeast cell, or other eukaryotic cells, such as COS cell, Chinese hamster ovary (CHO) cell, HeLa cell, HEK293 cell, COS-1 cell, NS0 cell or myeloma cell. In certain embodiments, the cell is a mammalian cell. In certain embodiments, the mammalian cell is HEK293T cell.

As used herein, the term "pharmaceutical composition" generally refers to a composition suitable for administration to a patient such as human patient. For example, the pharmaceutical composition described herein may comprise the nucleic acid molecule described herein, the vector described herein, and/or the cell described herein, and optionally a pharmaceutically acceptable adjuvant. In addition, the pharmaceutical composition may also comprise one or more (pharmaceutically effective) vehicles, stabilizers, excipients, diluents, solubilizers, surfactants, emulsifiers, and/or preservatives for suitable formulations. The acceptable ingredients of the composition are not toxic to recipients at the dosages and concentrations employed. The pharmaceutical composition of the present application includes, but is not limited to, liquid, frozen, and lyophilized compositions.

In the present application, the term "and/or" should be understood to mean either or both of the options.

As used herein, the term "comprise" or "include" generally means the inclusion of expressly specified features, but without the exclusion of other elements.

As used herein, the term "about" generally refers to variations above or below the specified value within the range of 0.5%-10%, such as variations above or below the specified value within the range of 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, or 10%.

DETAILED DESCRIPTION OF THE INVENTION

CYP4V2

In one aspect, the present application provides a vector which may comprise a polynucleotide encoding CYP4V2. In the present application, CYP4V2 may comprise a class of proteins whose dysfunctions or encoding gene mutations may lead to Bietti's crystalline dystrophy, including but not limited to CYP4V2 from human, chimpanzee, gorilla, rhesus monkey, dog, cow, mouse, rat, chicken, *drosophila*, nematode, or frog, or functional variants thereof. For example, the CYP4V2 may include human CYP4V2. In the present application, the polynucleotide encoding CYP4V2 may encode an amino acid sequence set forth in SEQ ID NO: 5. For example, the polynucleotide encoding CYP4V2 may encode an amino acid sequence having at least 90% identity to the amino acid sequence set forth in SEQ ID NO: 5, for example any amino acid sequence having at least 95%, at least 96%, at least 97%, at least 98%, or at least 99% identity to the amino acid sequence set forth in SEQ ID NO: 5.

In certain instances, the polynucleotide encoding CYP4V2 of the present application may comprise a synonymously mutated sequence of the polynucleotide naturally encoding CTP4V2. In certain instances, the polynucleotide encoding CYP4V2 of the present application may comprise a nucleotide sequence set forth in SEQ ID NO: 4. For example, the polynucleotide encoding CYP4V2 may comprise a nucleotide sequence having at least 90% identity to the nucleotide sequence set forth in SEQ ID NO: 4, for example any polynucleotide sequence having at least 95%, at least 96%, at least 97%, at least 98%, or at least 99% identity to the nucleotide sequence set forth in SEQ ID NO: 4.

The kozak sequence may be comprised at 5' end of the polynucleotide encoding CYP4V2 of the present application. For example, the kozak sequence may comprise a nucleotide sequence set forth in SEQ ID NO: 10 (gccacc).

Promoter

The vector of the present application may comprise a promoter. In the present application, the promoter may include a RPE cell-specific promoter, retinal cell-specific promoter, corneal cell-specific promoter, ocular cell-specific promoter, or constitutive promoter. The promoter may also include a mammalian beta-actin promoter or a viral promoter. The promoter may also include a CAG promoter (hybrid CMV early enhancer/chicken beta actin promoter, also known as CAGGS promoter, CB promoter, or CBA promoter), human beta actin promoter, small CBA (smCBA) promoter, CBS promoter or CBh promoter, elongation factor 1α short (EFS) promoter, elongation factor 1α (EF-1α) promoter, CMV promoter, PGK promoter, UBC promoter, GUSB promoter, UCOE promoter, VMD2 (also known as BEST1) promoter, OPEFS promoter, CYP4V2 native promoter, RPE65 promoter, or hybrids or derivatives thereof. For example, the promoter may be a CAG promoter.

For example, the promoter may comprise a nucleotide sequence set forth in SEQ ID NO: 2. For example, the promoter may comprise a nucleotide sequence having at least 90% identity to the nucleotide sequence set forth in SEQ ID NO: 2, for example any polynucleotide sequence having at least 95%, at least 96%, at least 97%, at least 98%, or at least 99% identity to the nucleotide sequence set forth in SEQ ID NO: 2.

In the present application, the promoter may be operably linked to the polynucleotide encoding CYP4V2. In certain instances, the promoter may be located at 5' end of the polynucleotide encoding CYP4V2.

The promoter described herein enables the efficient expression of the gene encoding the protein.

Polyadenylation (PolyA) Signal Site

In the present application, the vector may also comprise a polyadenylation (PolyA) signal site. The PolyA signal site may include SV40 signal site, BGH signal site, WPRE signal site, WPRE-SV40 signal site, WPRE-BGH signal site, or derivatives thereof.

In certain instances, the PolyA signal site can be recognized by a polyadenylation-related cleavage factor, leading to SV40 PolyA sequence, BGH signal PolyA sequence, HSV signal PolyA sequence, TK signal PolyA sequence, WPRE signal PolyA sequence, etc. For example, the PolyA signal site may be a BGH signal site, which may comprise a nucleotide sequence set forth in SEQ ID NO: 3. For example, the PolyA signal site may comprise a nucleotide sequence having at least 90% identity to the nucleotide sequence set forth in SEQ ID NO: 3, for example any polynucleotide sequence having at least 95%, at least 96%, at least 97%, at least 98%, or at least 99% identity to the nucleotide sequence set forth in SEQ ID NO: 3.

In certain instances, the polyadenylation signal site may be located at 3' end of the polynucleotide encoding CYP4V2.

Nucleic Acid Molecule

In one aspect, the present application provides a nucleic acid molecule, which may sequentially comprise, from 5' end to 3' end, a promoter, a polynucleotide encoding CYP4V2, and a PolyA signal site. For example, the promoter may comprise a nucleotide sequence set forth in SEQ ID NO: 2, the polynucleotide encoding CYP4V2 may comprise a nucleotide sequence set forth in SEQ ID NO: 4, and the PolyA signal site comprises a nucleotide sequence set forth in SEQ ID NO: 3. The kozak sequence (SEQ ID NO: 10) may be comprised at 5' end of the polynucleotide encoding CYP4V2.

In the present application, the nucleic acid molecule may comprise a nucleotide sequence set forth in SEQ ID NO: 11. For example, the nucleic acid molecule may comprise a nucleotide sequence having at least 80% (e.g., at least 80%, 85%, 90%, 99.1%, 99.2%, 99.3%, 99.4%, 99.5%, 99.6%, 99.7%, 99.8%, or 99.9%) sequence identity to the nucleotide sequence set forth in SEQ ID NO: 11.

Vector

The present application provides a vector comprising the nucleic acid molecule described herein.

In the present application, the vector may include plasmid, phagemid, cosmid, artificial chromosome (such as yeast artificial chromosome (YAC), bacterial artificial chromosome (BAC), or P1-derived artificial chromosome (PAC)), phage (such as λ phage or M13 phage), and viral vectors.

The vector described herein may include a viral vector. In certain instances, the viral vector may include retrovirus (including lentivirus), adenovirus, adeno-associated virus (AAV vector), herpesvirus (such as herpes simplex virus), poxvirus, baculovirus, papillomavirus, and papovavirus (such as SV40) vectors. The nucleic acid molecule may be comprised in the viral vector.

For example, the vector may include an AAV vector. The AAV vector gene may comprise an inverted terminal repeat (ITR) and an open reading frame (ORF), wherein the open reading frame may include a polynucleotide encoding Rep protein, and may also include a polynucleotide encoding a capsid. The AAV vector may also include a recombinant adeno-associated virus vector (rAAV vector).

In some cases, the vector may further comprise a restriction site downstream of the promoter to allow the insertion of a polynucleotide encoding the CYP4V2, wherein the promoter and restriction site may be located downstream of the 5' AAV ITR and upstream of the 3' AAV ITR. In some cases, the vector may further comprise a post-transcriptional regulatory element downstream of the restriction site and upstream of the 3' AAV ITR. In some cases, the vector may further comprise a polynucleotide inserted at the restriction site and operably linked to the promoter, wherein the polynucleotide may comprise the coding region of CYP4V2. As will be appreciated by those skilled in the art, any of AAV vectors disclosed in the present application can be used as a virus construct in the method to produce recombinant AAV.

In certain instances, one or more helper plasmids or helper viruses comprising adenoviral or baculoviral helper genes can provide helper functions. The non-limiting examples of adenoviral or baculoviral helper genes include, but are not limited to, E1A, E1B, E2A, E4, and VA, which can provide helper functions for AAV packaging.

The helper viruses for AAV are known in the art and can include, for example, viruses from Adenoviridae and Herpesviridae. It will be appreciated by those skilled in the art that any helper virus or helper plasmid for AAV that can provide sufficient helper functions for AAV can be used herein.

In some cases, the AAV cap gene can be present in the plasmid. The plasmid may also comprise the AAV rep gene. The rep gene and/or cap gene from any AAV serotype (including but not limited to AAV1, AAV2, AAV3, AAV3B, AAV4, AAV5, AAV6, AAV7, AAV8, AAV9, AAV10, AAV11, AAV12, AAV13, and any variant thereof) can be used herein to produce recombinant AAV. In some cases, the AAV cap gene can encode the capsid of serotype 1, serotype 2, serotype 3, serotype 3B, serotype 4, serotype 5, serotype 6, serotype 7, serotype 8, serotype 9, serotype 10, serotype 11, serotype 12, serotype 13, or variants thereof.

For example, the capsid, ITR, and other selected AAV components in the recombinant adeno-associated virus vector can be independently selected from any AAV, including but not limited to, AAV1, AAV2, AAV3, AAV4, AAV5, AAV6, AAV7, AAV8, AAV9, AAV8 bp, AAV7M8 and AAVAnc80, DJ, DJ/8, Rh10, variants of any known or mentioned AAV, or AAV yet to be discovered and variants or mixtures thereof.

In certain instances, the capsid sequence of the vector may be provided by another plasmid. For example, it may be provided by AAV-RC8, and its vector sequence may be set forth in SEQ ID NO: 9. For example, the capsid sequence may comprise a nucleotide sequence having at least 80% (e.g., at least 80%, 85%, 90%, 99.1%, 99.2%, 99.3%, 99.4%, 99.5%, 99.6%, 99.7%, 99.8%, or 99.9%) sequence identity to the nucleotide sequence set forth in SEQ ID NO: 9. In certain instances, the capsid sequence may further comprise amino acid mutations.

In certain instances, the AAV vector may be any one of AAV1, AAV2, AAV3, AAV4, AAV5, AAV6, AAV7, AAV8, AAV9, AAV8 bp, AAV7M8, AAVAnc80, DJ, DJ/8, and Rh10. For example, the AAV vector is an AAV vector having eye tissue-affinity, e.g., AAV2, AAV3, AAV4, AAV5, AAV8, DJ/8, or any rAAV vector.

In some cases, insect cells or mammalian cells can be transfected with helper plasmids or helper viruses, as well as virus constructs and plasmids encoding the AAV cap gene; and recombinant AAV viruses can be collected at various time points after cotransfection. For example, the recombinant AAV viruses are collected at about 12 hours, about 24 hours, about 36 hours, about 48 hours, about 72 hours, about 96 hours, about 120 hours after cotransfection, or at a time point between any two of these time points.

In certain instances, the AAV vector may be AAV2/2, AAV2/5, AAV2/8, or AAV2/9.

For example, the viral vector may include AAV2/8.

For example, the viral vector may comprise a vector backbone from AAV. The vector backbone may comprise a nucleotide sequence set forth in SEQ ID NO: 8.For example, the vector backbone may comprise a nucleotide sequence having at least 80% (e.g., at least 80%, 85%, 90%, 99.1%, 99.2%, 99.3%, 99.4%, 99.5%, 99.6%, 99.7%, 99.8%, or 99.9%) sequence identity to the nucleotide sequence set forth in SEQ ID NO: 8.

The recombinant AAV can also be produced by using any conventional method known in the art and suitable for producing the infectious recombinant AAV. In some cases, the recombinant AAV can be produced by using insect cells or mammalian cells that stably express some of the components necessary for AAV particle production. For example, a plasmid (or plasmids) comprising AAV rep and cap genes and a selection marker (such as kanamycin resistance gene) can be integrated into the genome of a cell. Then, the insect cells or mammalian cells can be co-transfected with a helper virus (such as adenovirus or baculovirus providing helper functions) and a virus vector comprising 5' AAV ITR and 3' AAV ITR (and, if desired, a nucleotide sequence encoding a heterologous protein). The advantage of this approach lies in that the cells are selectable and suitable for the large-scale production of recombinant AAV. As another non-limiting example, adenoviruses or baculoviruses can be used instead of plasmids to introduce the rep and cap genes into the cells for packaging. As yet another non-limiting example, both the virus vector comprising 5'AAV ITR and 3'AAV ITR and the virus vector comprising rep-cap genes can be stably integrated into the DNA of producer cells, and the helper functions can be provided by wild-type adenoviruses to produce recombinant AAV.

In certain instances, the vectors described in the present application may comprise a 5' non-coding region and/or a 3' non-coding region. The 5' non-coding region and/or 3' non-coding region may have various sequences. The exemplary 5' non-coding region has a nucleotide sequence set forth in SEQ ID NO: 6, and the exemplary 3' non-coding region has a nucleotide sequence set forth in SEQ ID NO: 7. In other cases, the vector described in the present application may not comprise the 5' non-coding region and/or 3' non-coding region.

The vector described in the present application may have a selection marker, which can include an antibiotic selection marker. For example, the antibiotic selection marker can include a kanamycin selection marker.

Figure 22:
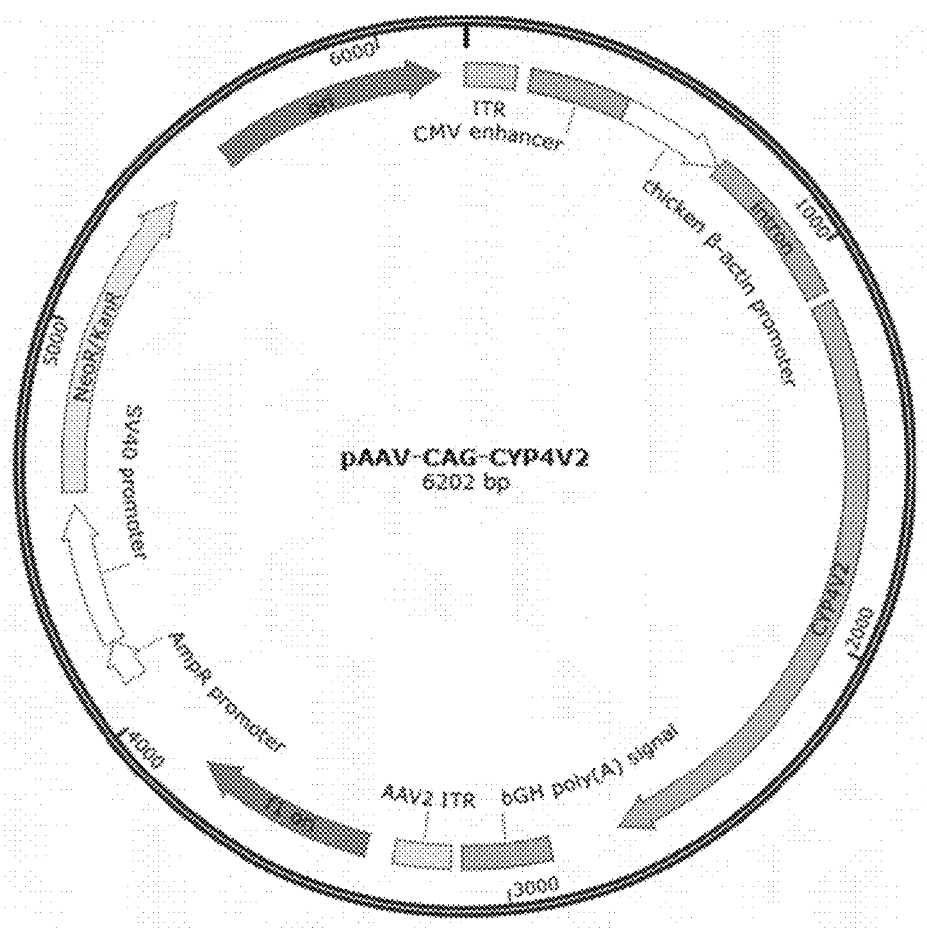
FIG. 22 shows a schematic diagram of pAAV-CAG-CYP4V2 vector.

For example, the vector described in the present application may comprise a map as shown in FIG. 22. For example, the vector described herein may comprise a nucleotide sequence set forth in SEQ ID NO: 1. For example, the vector may comprise a nucleotide sequence having at least 90% homology to the nucleotide sequence set forth in SEQ ID NO: 1, for example any polynucleotide sequence having at least 95%, at least 96%, at least 97%, at least 98%, or at least 99% homology to the nucleotide sequence set forth in SEQ ID NO: 1.

The vector described in the present application can be administrated to the eye by retinal or vitreous administration. Among the possible modes of administration, the vector can be administrated as an injectable liquid. For example, the vector can be administrated as an injectable liquid by means of a capsule or syringe.

Kit

The present application provides a kit, which can include the nucleic acid molecule or vector described in the present application. The kit described in the present application may also include buffers and/or pharmaceutically acceptable adjuvants. As well known in the art, the pharmaceutically acceptable adjuvants are relatively inert substances which facilitate the administration of the pharmacologically effective substance and which may be provided as liquid solutions or suspensions, as emulsions, or as solid forms suitable for dissolution or suspension in the liquid prior to use. For example, the adjuvant may afford the form or consistency or act as a diluent. Suitable adjuvants may include, but not limited to, stabilizers, lubricants, or emulsifying agents, salts for altering the osmotic pressure, encapsulating agents, pH buffering substances, and buffers. For example, the adjuvant can include an agent suitable for direct delivery to the eye, which can be administrated without undue toxicity. The pharmaceutically acceptable adjuvants can include, but not limited to, liquids such as water, saline, glycerol, and ethanol. The pharmaceutically acceptable salts may also be encompassed, including but not limited to inorganic salts such as hydroxides, hydrobromides, phosphates, and sulfates; and organic salts such as acetates, propionates, and benzoates.

In the protocol involving the subretinal injection, the pharmaceutically acceptable adjuvant may include a pharmaceutically acceptable vehicle. The pharmaceutically acceptable vehicles can be sterile liquids, such as water and oils, including those of petroleum, animal, vegetable, or synthetic origin, such as peanut oil, soybean oil, and mineral oil. The saline solutions as well as aqueous dextrose, polyethylene glycol, and glycerol solutions can also be employed as liquid carriers, particularly injectable solutions. Additional ingredients such as preservatives, buffers, isotonic agents, antioxidants and stabilizers, nonionic wetting or clarifying agents, and solubilizers may also be used. The kit described in the present application can be packaged in a single unit dose or multi-dose form. The contents of the kit are generally configured as sterile and substantially isotonic solutions.

In the present application, the vector comprising the nucleic acid molecule may be present in the same or a different excipient as other components (e.g., helper plasmid or helper virus comprising a sequence encoding the capsid).

The kit described in the present application may further include other materials required from the commercial and user standpoints, including other buffers, diluents, filters, pillows, syringes, and instruction inserts for implementing any of the methods described in the present application. Suitable packaging materials may also be included and may be any packaging material consistent in the art, such as vials, ampoules, cans, flexible packaging. These articles can be further sterilized and/or sealed. The kit of the present application may also include instructions, dosing regimen, one or more thin needles, one or more syringes, and solvents.

Cell

The present application also provides a cell, wherein the cell may comprise the vector described herein. In certain instances, the cell may be a cell in which the vector is expressed. In certain instances, the cell may include the progeny of a single cell. The progeny may not necessarily be completely identical to the original parent cell (either morphologically in total DNA complement, or genomically). For example, the cell may further include a cell transfected in vitro with the vector described herein. In certain instances, the cell may include bacterial cell (e.g., *E. coli*), yeast cell, or other eukaryotic cells, such as COS cell, Chinese hamster ovary (CHO) cell, HeLa cell, HEK293 cell, COS-1 cell, NS0 cell or myeloma cell, and 293T cell. In certain instances, the cell is a cell from a patient with Bietti's crystalline dystrophy. For example, the cell may include somatic or stem cell.

The cell described herein may include retinal cell, corneal cell, choroidal cell, lens cell, nerve cell, RPE cell, and stem cell, and the stem cell may include induced pluripotent stem cell (iPSC), embryonic stem cell (ESC), mesenchymal stem cell (MSC), adult stem cell, or any cell differentiated from stem cell. For example, the retinal cell, corneal cell, choroidal cell, lens cell, nerve cell, or RPE cell can be induced and differentiated from the stem cell. Also, for example, the cell may include ARPE-19 cell, or human iPSC-induced RPE cell.

Pharmaceutical Composition

In another aspect, the present application provides a pharmaceutical composition comprising said vector and/or said cell. The pharmaceutical composition may also comprise optionally pharmaceutically acceptable adjuvant. In certain instances, the pharmaceutical composition described herein may also comprise one or more (pharmaceutically effective) vehicles, stabilizers, excipients, diluents, solubilizers, surfactants, emulsifiers, and/or preservatives for suitable formulations.

In certain instances, the acceptable ingredients of the composition are not toxic to recipients at the dosages and concentrations employed. In certain instances, the pharmaceutical composition includes, but is not limited to, liquid, frozen, and lyophilized compositions. In certain instances, the pharmaceutically acceptable adjuvant may include any and all solvents, dispersion media, coatings, isotonic agents, and absorption delaying agents compatible with the pharmaceutical administration, which are generally safe, non-toxic, and neither biologically nor otherwise undesirable.

For example, the pharmaceutical composition may involve parenteral, transdermal, intracavity, intraarterial, intrathecal, and/or intraocular administration, or direct injection into tissues.

For example, the pharmaceutical composition may be administrated to a patient or subject by instillation, infusion, or injection. For example, the pharmaceutical composition may be uninterruptedly (or continuously) administrated. For example, the uninterrupted (or continuous) administration may be achieved by a small pump system worn by a patient for measuring the influx of the therapeutic agent into the patient, as described in WO2015/036583.

In the present application, the subject may include human and non-human animals. For example, the subject may include, but not limited to, cats, dogs, horses, pigs, cows, sheep, rabbits, mice, rats, or monkeys.

Treatment Method

In another aspect, the present application provides a method for treating, alleviating, and/or preventing a disease or disorder associated with retinal pigment epithelium (RPE) atrophy, using said nucleic acid molecule, vector, pharmaceutical composition, kit, or cell. In certain instances, the disease or disorder includes retinal degeneration.

In certain instances, the retinitis pigmentosa may include uniocular primary retinitis pigmentosa, sector primary retinitis pigmentosa, central or paracentral primary retinitis pigmentosa, retinitis pigmentosa sine pigmento, albescent punctate degeneration of retina, Bietti's crystalline dystrophy, pigmented paravenous retinitis pigmentosa, preserved para-arteriolar retinal pigment epithelium retinitis pigmentosa, Leber congenital amaurosis, and retinitis pigmentosa in other syndromes. For example, the retinitis pigmentosa may include Bietti's crystalline dystrophy.

For example, the Bietti's crystalline dystrophy may include a disease caused by CYP4V2 gene mutation.

In certain instances, the CYP4V2 gene mutation may include, but not limited to, missense mutation, replication error, splice site error, frameshift, base deletion or insertion, nonsense mutation, polymorphism (e.g., single nucleotide polymorphism), premature termination, partial or whole deletion of CYP4V2 gene, and unidentified CYP4V2 gene variations associated with Bietti's crystalline dystrophy.

For example, the CYP4V2 gene mutation may include the mutations shown in Table 2:

TABLE 2

Certain types of CYP4V2 gene mutations

| Exon or intron position | Nucleic acid change | Predicted protein change |
|---|---|---|
| 1 | c.31C > T | p.Q11X |
| 1 | c.64C > G | p.L22V |
| 1 | c.71T > C | p.L24P |
| 1 | c.77G > A | p.G26D |
| 1 | c.130T > A | p.W44R |
| 1 | c.134A > C | p.Q45P |
| 1 | c.181G > A | p.G61S |
| 1 | c.197T > G | p.M66R |
| IVS1 | c.214 + 1G > A | Exon 1 deletion |
| IVS1 | c.214 + 25delT | 未知 |
| IVS1 | c.215 − 2A > G | Exon 2 deletion |
| IVS1 | c.215 − 1G > A | Exon 2 deletion |
| 2 | c.219T > A | p.F73L |
| 2 | c.237G > T | p.E79D |
| 2 | c.253C > T | p.R85C |
| 2 | c.277T > C | p.W93R |
| 2 | c.283G > A | p.G95R |
| 2 | c.327G > A | Unknown |
| IVS2 | c.327 + 1G > A | p.E72Gfs*5 |
| IVS2 | c.327 + 11G > C | Unknown |
| 3 | c.332T > C | p.I111T |
| 3 | c.335T > G | p.L112* |
| 3 | c.367A > G | p.M123V |
| 3 | c.400G > T | p.G134* |
| 3 | c.413 + 2T > G | Splicing acceptor |
| 4 | c.518T > G | p.L173W |
| 5 | c.637_641delAGTAA | p.S213* |
| 5 | c.655T > C | p.Y219H |
| 6 | c.677T > A | p.M226K |
| 6 | c.694C > T | p.R232* |
| 6 | c.724delG | p.D242Ifs*35 |
| 6 | c.732G > A | p.W244* |
| 6 | c.761A > G | p.H254R |
| 6 | c.772C > T | p.L258F |
| 6 | c.791delT | Deletion |
| 7 | c.802 − 8_806dell3 | Exon 7 deletion |
| 7 | c.802 − 8_810dell7insGC | Exon 7 deletion |
| 7 | c.810delT | p.(N271Rfs*34) |
| 7 | c.838G > T | p.E280* |
| 7 | c.958C > T | p.R320* |
| 7 | c.971A > T | p.D324V |
| 7 | C.974C > T | p.T325I |
| IVS7 | c.985 + 3A > G | Unknown |
| 8 | c.992A > C | p.H331P |
| 8 | C.998C > A | p.T333K |
| 8 | c.1020G > A | p.W340* |
| 8 | c.1021T > C | p.S341P |
| 8 | c.1027 T > G | p.Y343D |
| 8 | c.1062dupA | p.V355Sfs*4 |
| IVS8 | c.1091 − 2A > G | Exon 9 deletion |
| 9 | c.1157A > C | p.K386T |
| 9 | c.1168C > T | p.R390C |
| 9 | c.1169G > A | p.R390H |
| 9 | c.11780T | p.P393L |
| 9 | c.11870T | p.P396L |
| 9 | c.1198C > T | p.R400C |
| 9 | c.11990A | p.R400H |
| 9 | c.1219G > T | p.E407* |
| 9 | c.1225 + 1 G > A | p.(G364_V408del) |
| 10 | c.1226 − 6_1235dell6 | Exon 10 deletion |
| 10 | c.1328G > A | p.R443Q |
| 10 | c.13480T | p.Q450* |
| 10 | c.1355G > A | p.R452H |
| 10 | c.1372G > A | p.V458M |
| 10 | c.1393A > G | p.R465G |
| 10 | c.1396 A > G | p.N466D |
| 10 | c.1399T > C | p.C467R |
| 10 | c.1441delT | p.(S481Rfs*4) |
| 10 | c.1445C > T | p.S482* |
| 11 | c.1523G > A | p.R508H |
| 11 | c.1526C > T | p.P509L |

Without intention to be limited by any theory, the following Examples are only intended to illustrate the fusion proteins, preparation methods, uses, etc. in the present application, and are not intended to limit the scope of the claimed invention. The Examples do not include detailed descriptions of conventional methods, such as methods for constructing vectors and plasmids, methods for inserting the genes encoding proteins into such vectors and plasmids, or methods for introducing plasmids into host cells. Such methods are well known to those of ordinary skill in the art, and are described in numerous publications, including Sambrook, J., Fritsch, E. F. and Maniais, T. (1989) Molecular Cloning: A Laboratory Manual, 2nd edition, Cold spring Harbor Laboratory Press. The unspecified chemical reagents can be purchased through conventional commercial channels.

EXAMPLE

Example 1 Vector Construction

Construction of vector pAAV-CAG-CYP4V2 (synthesized by Genewiz Inc., Suzhou, China): the vector backbone was pAAV plasmid, wherein ITR sequence was from AAV2, and the vector structure between two ITRs was shown in FIG. 1, comprising a promoter, coding region, and terminator polyA signal. The coding region comprises a nucleotide sequence encoding the CDS of human-derived wild-type CYP4V2. The kozak sequence was added at 5' end of CDS to promote the translation. The promoter in the vector was CAG, with a nucleotide sequence set forth in SEQ ID NO: 2; the kozak sequence was set forth in SEQ ID NO: 10; the nucleotide sequence encoding the CDS of human-derived CYP4V2 was set forth in SEQ ID NO: 4; the terminator polyA BGH had a nucleotide sequence set forth in SEQ ID NO: 3; and the backbone vector had a nucleotide sequence set forth in SEQ ID NO: 8.

Construction of AAV vectors with different promoters: different promoters, namely CMV (SEQ ID NO: 16), EFS (SEQ ID NO: 18) and EF1a (SEQ ID NO: 17), were used to replace CAG promoter for the expression of CYP4V2.

Construction of AAV vectors with CAG promoter variants: different variants for CAG promoter, namely CAG-M1 (SEQ ID NO: 19), CAG-M2 (SEQ ID NO: 20) and CAG-M3 (SEQ ID NO: 21), were used to replace CAG promoter for the expression of CYP4V2.

Construction of AAV vectors with different terminators: different terminators, namely SV40 (nucleotide sequence set forth in SEQ ID NO: 12), WPRE (nucleotide sequence set forth in SEQ ID NO: 13), WPRE-SV40 (nucleotide sequence set forth in SEQ ID NO: 14) and WPRE-BGH (nucleotide sequence set forth in SEQ ID NO: 15), were used to replace BGH terminator for the expression of CYP4V2.

Additional constructions of reporter vectors with different promoters or different terminators: GFP CDS as reporter gene was linked at 3' end of CYP4V2 CDS sequence in the corresponding AAV vector to construct the reporter vector.

Each fragment was cloned and inserted into the vector, and the obtained virus vector was transformed into *E. coli* competent cells. After shaking culture and sequencing, the plasmid was extracted using Plasmid Midi Kit (Omega, D6915-04).

Example 2 AAV Packaging and Purification (1) Virus Packaging

Day 0: Cell seeding (seeding number: $1\times10^7$): 293T cells were seeded in a 15 cm dish. Day 1: When 293T cells reached 80%-90% confluence, the medium was refreshed with 20 ml of complete medium (Gibco, C11965500BT) containing 10% serum (Shanghai ExCell, FSP500) for plasmid transfection. Day 2: 12-18 hours after transfection, the medium was refreshed with 30 ml of fresh complete medium. Day 3: 48 hours after transfection, the medium was replaced with 30 ml of fresh complete medium. Day 4: 72 hours after transfection, 293T cells were trypsinized according to the conventional method, collected into a 50 ml centrifuge tube, washed twice with PBS, centrifuged at 1200 rpm for 5 min, and frozen at −80° C. refrigerator after removing PBS.

(2) Virus Purification

The AAV293T cells obtained by packaging were thawed. The cells were resuspended with cell lysis buffer (150 mM NaCl, 50 mM Tris, pH8.5). Half volume (3 ml, relative to the cell lysate) of chloroform was added to the centrifuge tube, the tube cap was tightened, and the tube was horizontally placed on a shaker at 37° C. and shaken at 250 rpm for 30 min. 5M sodium chloride was added and mixed well, transferred to a high-speed centrifuge tube, and centrifuged at 11,000 rpm for 25 min. The upper aqueous phase was taken. The part at the interface that was difficultly pipetted was transferred to a 1.5 ml centrifuge tube, and centrifuged at 12,000 rpm for 30 s. The supernatants were combined. The nuclease (Benzonase) was added to the upper aqueous phase to a final concentration of 50 U/ml, the sodium deoxycholate was added to a final concentration of 0.4%, and the following were added to their respective final concentrations: 10 mM of $MgCl_2$, 0.5 mM of $CaCl_2$, 5 IU/ml of Turbo DNase I, 25 ug/ml of RNaseA (stock solution concentration: 10 mg/ml). 37° C. water bath was conducted for 30 min. 50% PEG8000 was added, mixed well by shaking, placed on ice for 1 hour, and centrifuged at 11,000 rpm for 25 min. The supernatant was aspirated and discarded, and the remaining was centrifuged again for 1 min to remove the residual supernatant. PBS was added according to the final dissolving volume requirement, suspended by pipetting, and transferred to a 1.5 ml centrifuge tube. 500 μl of chloroform was added, shaken, and centrifuged at 12,000 rpm for 20 min. The supernatant was pipetted under sterile conditions, and stored in aliquots at −80° C.

Example 3 Estimation of Promoter Strength Using EGFP as a Reporter Gene

The reporter vector plasmids with different promoters were transfected into 293T cells (ATCC™, CRL-3216), respectively. The details were as follows: 293T cells (ATCC™, CRL-3216) were plated onto a 35 mm dish on the first day, and reached to about 70% confluence on the second day. The transfection system was formulated as follows: to 100 μl of serum-free DMEM, 2 μg of the plasmid obtained in Example 2 and 3 μl of PEI were added respectively and mixed well, to stand for 20 min; the obtained transfection system was added to the cell medium, shaken well, and placed in a CO2 incubator; and the medium was replaced after 6 h or overnight. The fluorescence signal was observed by fluorescence microscope (Life AMF4305) after 24 hours.

The results were shown in FIGS. 2A and 2B. The vectors with different promoters all could express GFP, and the expression strength ranking was as follows: CAG~EF1a>CMV>EFS; CAG>CAG-M2~CAG-M3>CAG-M1.

Example 4 Estimation of Promoter Strength by CYP4V2 Expression

The reporter vector plasmids with different promoters were transfected into 293T cells (ATCC™, CRL-3216), respectively. After 48 hours, the cells were lysed with RIPA lysis buffer (Beijing Applygen C1053-100) for running in the gel. The expression of CYP4V2 was detected by Western blotting. The following antibodies were used: anti-CYP4V2 (Atlas™, HPA029122), anti-actin (Abclonal™, AC026), goat-anti-rabbit (Abclonal™, AS014). The fluorescence signal was observed by fluorescence microscope (Life AMF4305) after 24 hours.

The results were shown in FIG. 3. The vectors with different promoters all could express CYP4V2. The CAG and EF1a promoters showed good expression effects, followed by the CMV promoter, and the EFS promoter was the weakest.

Example 5 Estimation of Terminator Strength Using EGFP as Reporter Gene

Construction of AAV vectors with different terminators in accordance with the procedure in Example 1: different terminators, namely SV40 (nucleotide sequence set forth in SEQ ID NO: 12), BGH (nucleotide sequence set forth in SEQ ID NO: 3), WPRE (nucleotide sequence set forth in SEQ ID NO: 13), WPRE-SV40 (nucleotide sequence set forth in SEQ ID NO: 14), and WPRE-BGH (nucleotide sequence set forth in SEQ ID NO: 15) were used to construct the virus vectors comprising CAG promoter, CYP4V2 CDS sequence, and terminator, respectively. GFP CDS as reporter gene was linked at 3' end of CYP4V2 CDS sequence to construct the reporter vectors with different promoters. The gene synthesis and subcloning here were accomplished by Beijing Tsingke Biotechnology.

The different vectors as above were transfected into 293T cells (ATCC™, CRL-3216), respectively, and the fluorescence signal was observed by fluorescence microscope (Life AMF4305) after 24 hours.

Figure 4:
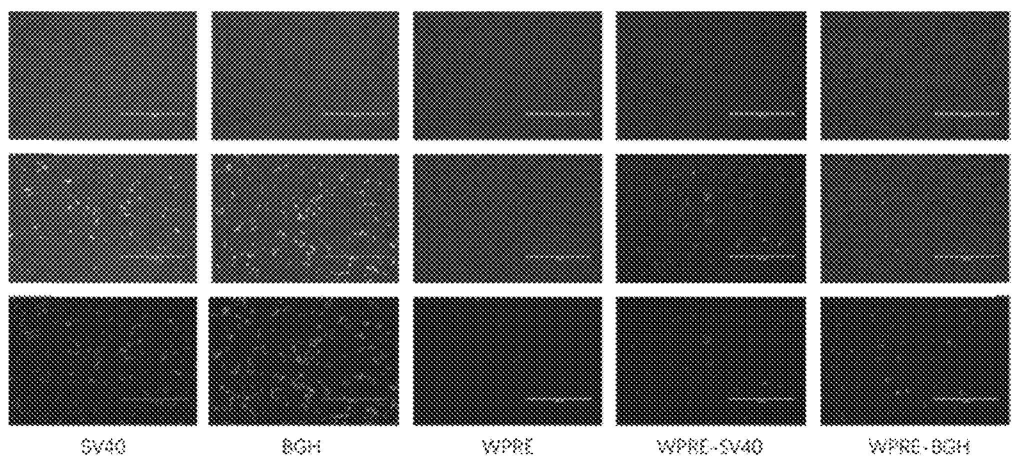
FIG. 4 shows the GFP fluorescence intensities of vectors with different polyadenylation signal sites.

The results were shown in FIG. 4. The BGH terminator and SV40 terminator showed good expression effects, WPRE showed the weakest expression effect, and WPRE-BGH and WPRE-SV40 showed moderate expression effects.

Example 6 Estimation of Terminator Strength by CYP4V2 Expression

The reporter vectors with different terminators as constructed in Example 5 were transfected into 293T cells (ATCC™, CRL-3216), respectively. After 48 hours, the cells were lysed with RIPA lysis buffer (Beijing Applygen C1053-100) for running in the gel. The expression of CYP4V2 was detected by Western blotting. The following antibodies were used: anti-CYP4V2 (Atlas™, HPA029122), anti-actin (Abclonal™, AC026), goat-anti-rabbit (Abclonal™, AS014).

Figure 5:
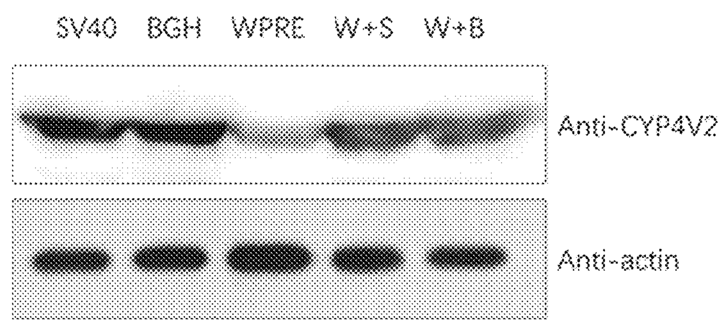
FIG. 5 shows the CYP4V2 protein expressions of vectors with different polyadenylation signal sites.
Figure 6A:
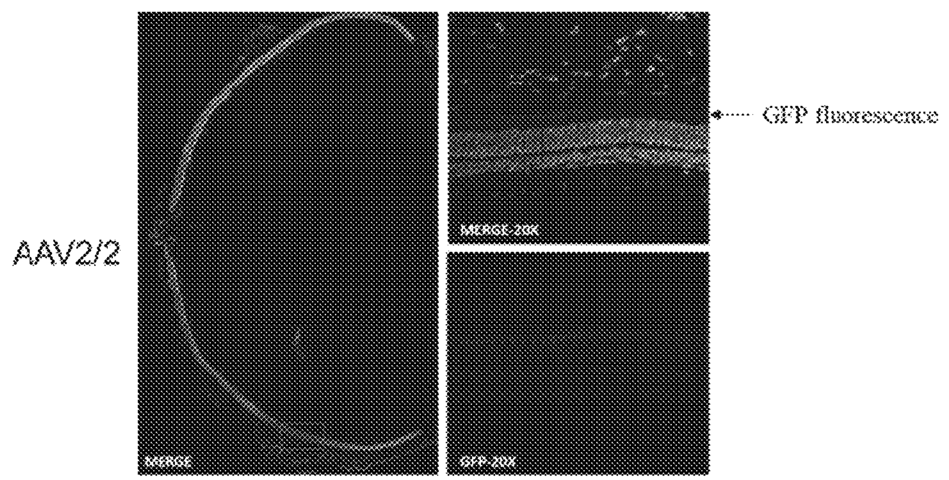
Figure 6B:
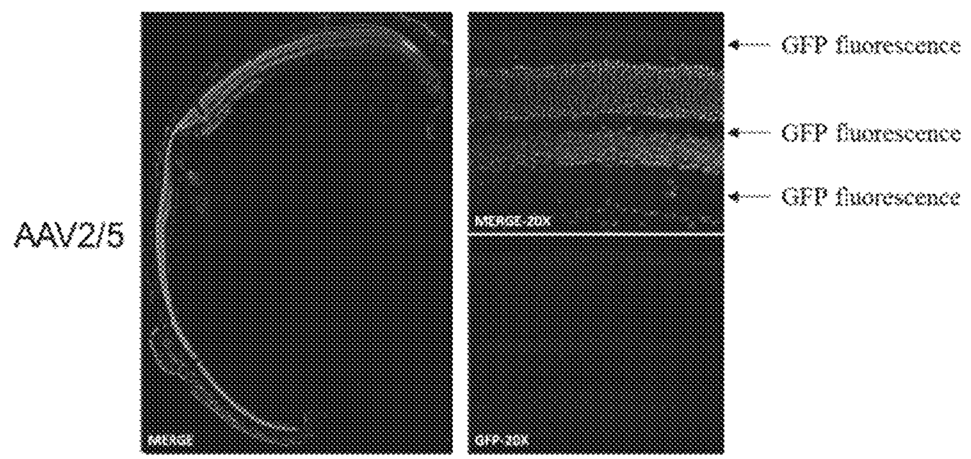
Figure 6C:
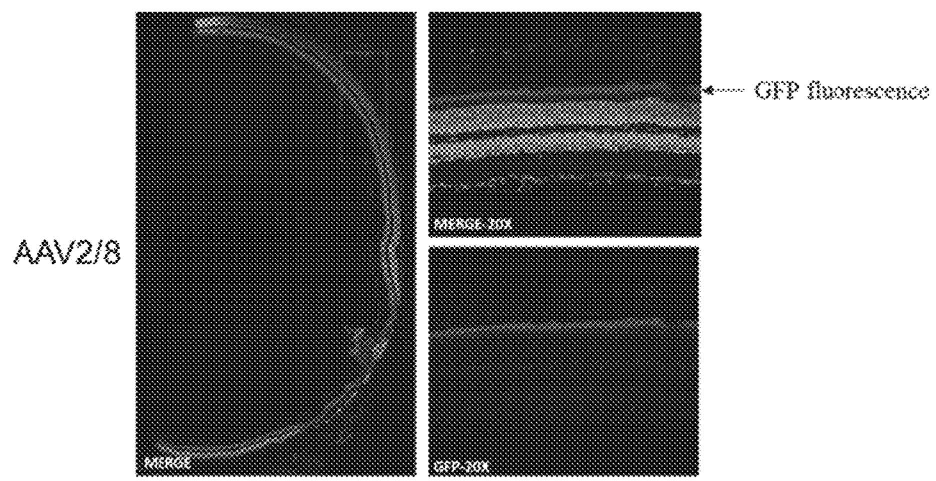
Figure 6D:
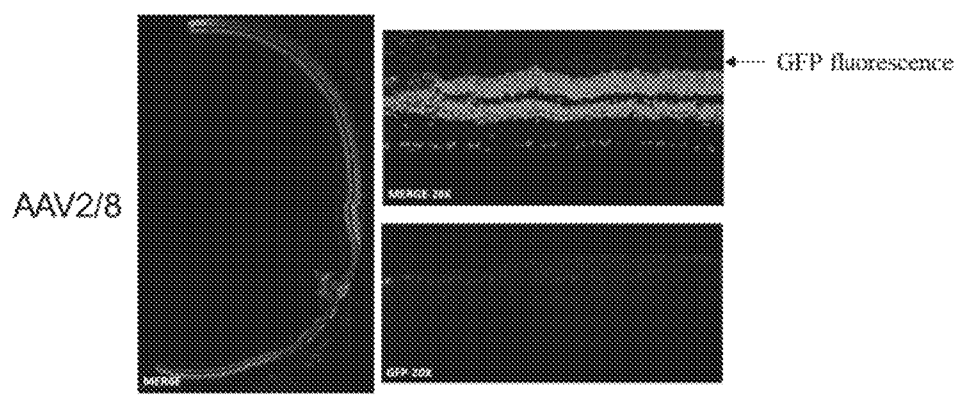
Figure 6E:
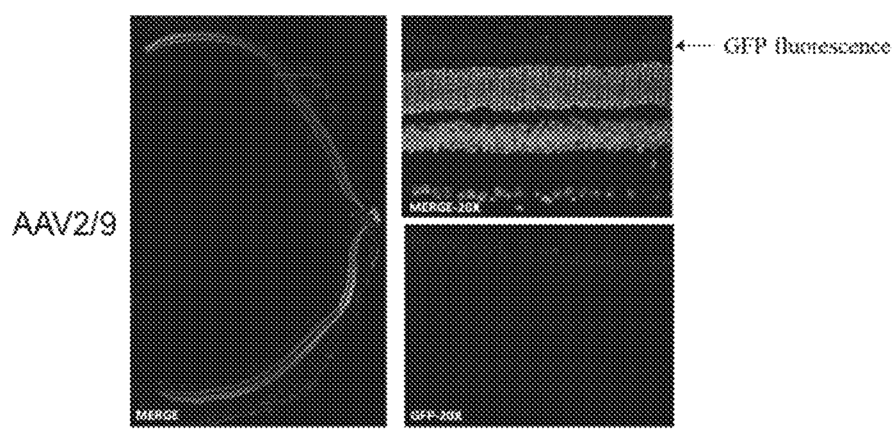
Figure 6F:
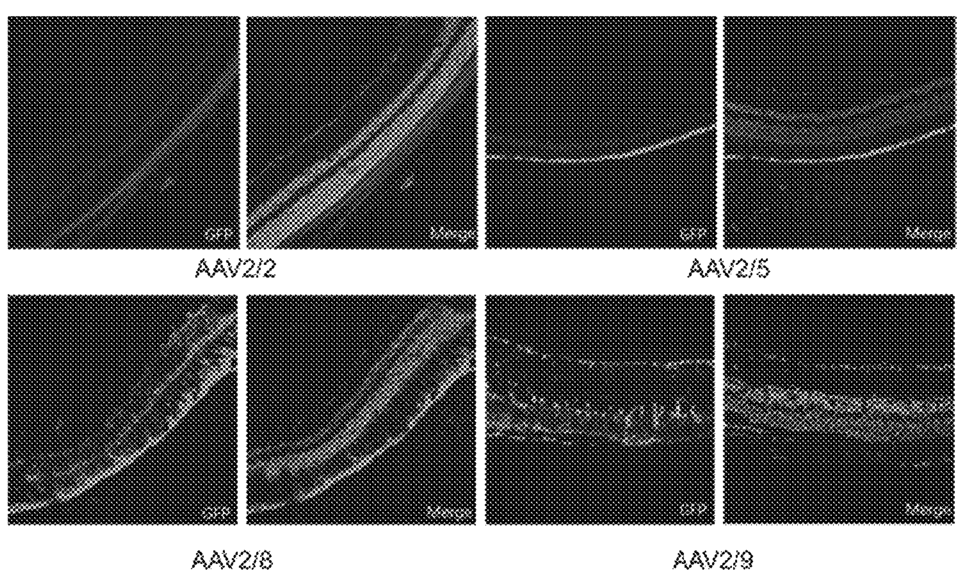
FIG. 6F: local detections of four AAV serotypes at 1 month after injection.

The results were shown in FIG. 5. The BGH terminator and SV40 terminator showed good expression effects, WPRE showed the weakest expression effect, and WPRE-BGH and WPRE-SV40 showed moderate expression effects.

Example 7 Selection of AAV Capsid Serotype (CMV Promoter)

The viruses of AAV2/2, AAV2/5, AAV2/8, and AAV2/9 serotypes packaging GFP reporter gene and having CMV as promoter (purchased from Shandong Weizhen Biotechnology Co., Ltd.) were subretinal injected ($1\times10^9$ vg/eye, 1 μL) in wild-type mice (C57BL/6J mice, 4-8 weeks old, purchased from Charles River), respectively. 1 week or 1 month after the injection, the retinal histomorphology was observed by embedding sections. The GFP protein fluorescence indicated the expression site of the vector, and the cell nucleus was labeled by DAPI.

As can be seen from FIGS. 6A to 6F, at the time of 1 week after injection, the expression of capsid protein serotype AAV8 was the strongest, and the expressions of AAV2, AAV5, and AAV9 could also be detected. At the time of one month after injection, AAV2 and AAV5 had moderate fluorescence intensities, mainly in RPE cells and photoreceptor cells; AAV8 and AAV9 showed good effects, specifically infecting the outer segments of photoreceptor cells as well as RPE cells, and also expressed in outer nuclear layer and bipolar cells. The GFP fluorescence expression intensity ranking was as follows: AAV8>AAV9>AAV5>AAV2.

Thus, AAV8 had the fastest expression speed and more stable expression intensity.

Example 8 Selection of AAV Capsid Serotype (CAG Promoter)

The viruses of AAV2/2, AAV2/5, AAV2/8, and AAV2/9 serotypes packaging GFP reporter gene and having CAG as promoter (purchased from Shandong Weizhen Biotechnology Co., Ltd.) were subretinal injected ($1\times10^9$ vg/eye, 1 μL) in wild-type mice (C57BL/6J mice, 4-8 weeks old, Charles River). 1 month after injection, the retinal histomorphology was observed by embedding sections. The GFP protein fluorescence indicated the expression site of the vector, and the cell nucleus was labeled by DAPI.

Figure 7:
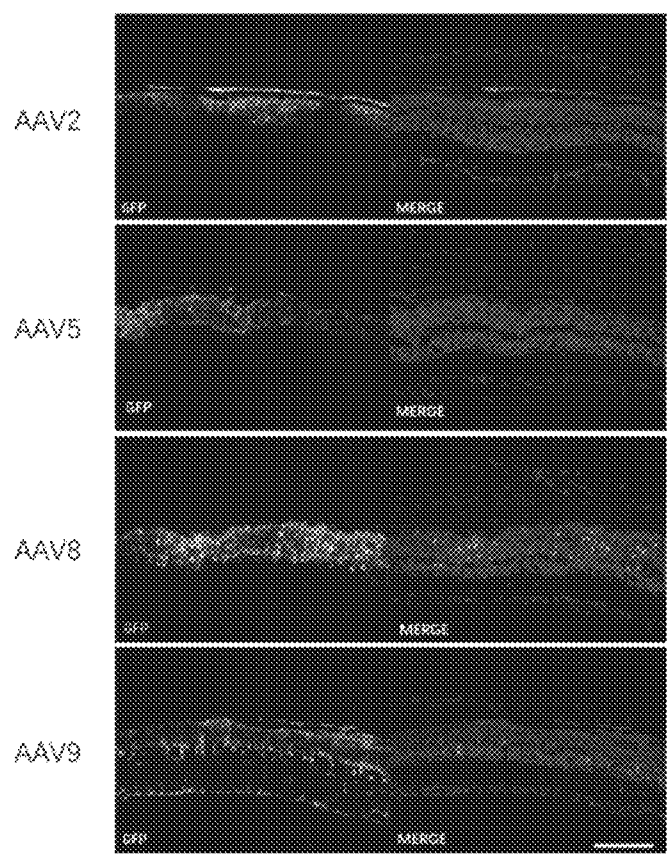
FIG. 7 shows the expressions of different serotypes of AAVs using the CAG promoter in mouse retina at 1 month after injection, wherein: A: AAV2; B: AAV5; C and D: AAV8; E: AAV9; F: local detections of four AAV serotypes.

As can be seen from FIG. 7, at the time of one month after injection, AAV2 and AAV5 had moderate fluorescence intensities, mainly in RPE cells and photoreceptor cell layer; AAV8 had relatively strong fluorescence intensity, specifically infecting photoreceptor cells and RPE cells; AAV9 had the strongest fluorescence intensity, expressed in bipolar cells and optic nerve cell layer in addition to infecting photoreceptor cells and RPE cells. The GFP fluorescence expression intensity ranking was as follows: AAV9>AAV8>AAV5-AAV2.

Thus, AAV8 had the strongest expression intensity, and the infected cell types were more specific.

Example 9 Construction and Packaging of AAV8 Virus Vectors with Different Promoters 9.1 Construction of AAV2/8 Vector pAAV-RC8-Kana (i.e., AAV2/8) was obtained through the engineering based on pAAV-RC5-Amp (purchased from Beijing XMJ Scientific Co., Ltd.), wherein the sequence of the vector was set forth in SEQ ID NO: 9.

9.2 Packaging and Purification (1) Virus Packaging

The packaging and purification were conducted in accordance with the procedure in Example 2, and the specific transfection system was shown in Table 3.

TABLE 3

| Transfection system | |
|---|---|
| System components | per 15 cm dish |
| Expression vector | CYP4V2 expression vectors packaging GFP reporter gene and having different promoters |
| AAV-helper | 15 μg |
| AAV2/8 | 15 μg |
| Plasmid mix | 45 μg |

TABLE 3-continued

| Transfection system | |
|---|---|
| System components | per 15 cm dish |
| Serum-free DMEM (Gibco, C11965500BT) | 2000 μl |
| PEI (Polysciences 24765-1) | 135 μl |

AAV8 virus vectors with different promoters were obtained.

Example 10 Effect of Infection by AAV8 Viruses with Different Promoters on Human iPSC Derived RPE Cells The human induced pluripotent stem cells (iPSCs) were purchased from Beijing Cellapy. In accordance with the process described in the literature (da Cruz, L., et al., (2018), Phase 1 clinical study of an embryonic stem cell-derived retinal pigment epithelium patch in age-related macμlar degeneration, Nat Biotechnol 36(4): 328-337), RPE cells were produced. The human iPSCs ($3\times10^4/cm^2$) were cultured in 4 ml of TESR-E8 medium (STEMCELL, CAT #05990, #05991) in a T25 flask. The medium was replaced with 6 ml of medium (Gibco, CAT #10829018) containing 20% serum substitute (Gibco, CAT #A3181502) after 5 days, and then replaced with 6 ml of serum-free medium (Gibco, CAT #10829018) after culturing for 2 days. The culture was continued for about 20 weeks, to obtain elliptical and dark dividable cells, i.e., RPE cells.

Figure 8:
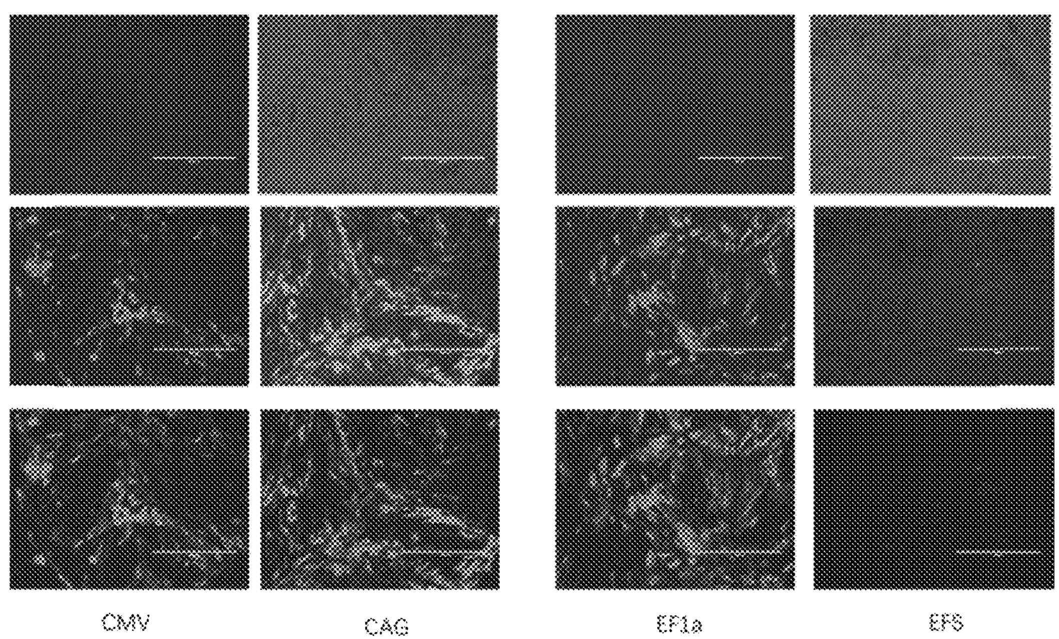
FIG. 8 shows the effects of infecting with AAV8 viruses with different promoters on RPE cells induced and differentiated from iPSCs.

The same amounts of RPE cells were infected with viruses of AAV2/8 serotype packaging GFP reporter gene and having different promoters in Example 9 (MOI=$1\times10^6$), and the fluorescence signal was observed by fluorescence microscope (Life AMF4305) after 10 days. The results were shown in FIG. 8. The virus vector using the CAG promoter showed a good fluorescent protein expression effect, followed by the CMV promoter, then followed by the EF1a promoter, and the EFS promoter was the weakest.

Example 11 Effect of Infection by AAV8 Viruses with Different Promoters on Human iPSC Derived 3D-Retinal Organoids Referring to Zhong, X., Gutierrez, C., Xue, T. et al. Generation of three-dimensional retinal tissue with functional photoreceptors from human iPSCs. *Nat Commun* 5, 4047 (2014), the 3D-retinal organoids were differentiated from human induced pluripotent stem cells (iPSCs).

Figure 9:
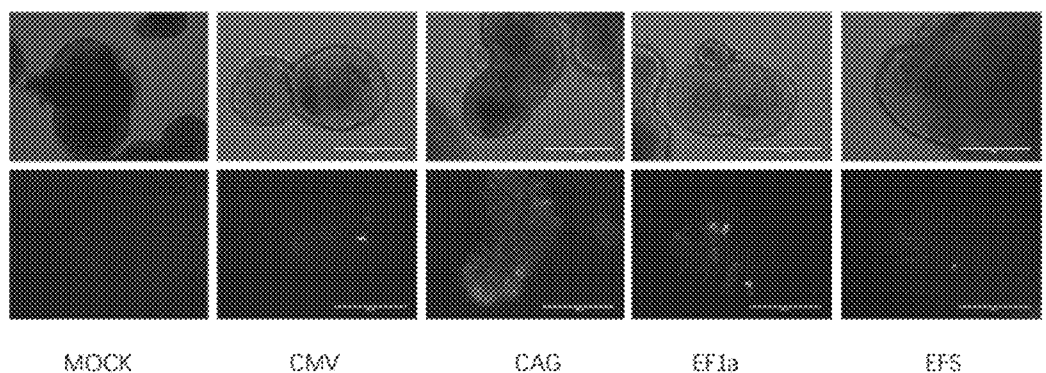
FIG. 9 shows the effects of infecting with AAV8 viruses with different promoters on the 3D-retinal organoid induced and differentiated from iPSCs.

The 3D-retinal organoids in a 96-well plate were infected with viruses of AAV2/8 serotype packaging GFP reporter gene and having different promoters in Example 9 (virus titer: $5\times10^{10}$/cup). The fluorescence signal was observed by fluorescence microscope (Life AMF4305) after 14 days. The results were shown in FIG. 9. The virus vector using the CAG promoter showed a good fluorescent protein expression effect.

Example 12 Expressions of AAV8 Viruses with Different Promoters by Subretinal Injection in Mice The viruses of AAV2/8 serotype packaging GFP reporter gene and having different promoters in Example 9 were subretinal injected ($1\times10^9$ vg/eye, 1 μL) in wild-type mice (C57BL/6J mice, 4-8 weeks old, Charles River). 2 weeks or 6 weeks after injection, the retinal histomorphology was observed by embedding sections. The GFP fluorescence indicated the expression site of the vector, and the cell nucleus was labeled by DAPI.

Figure 10A:
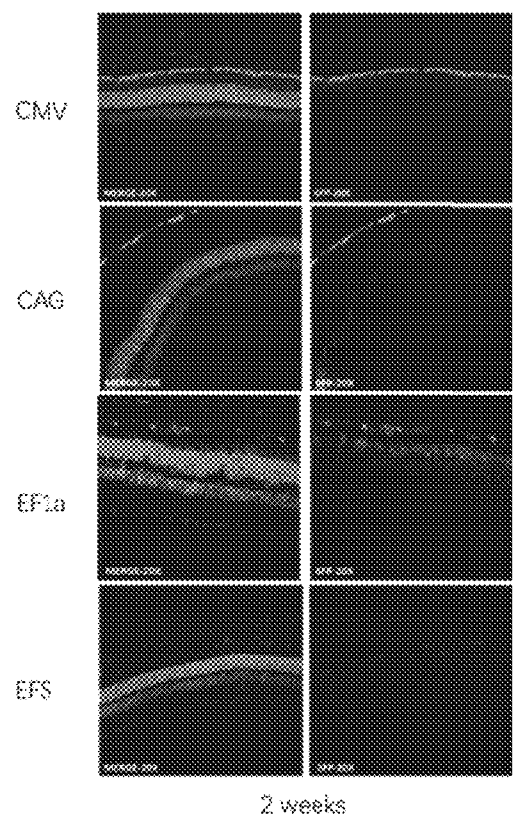
FIG. 10A and FIG. 10B show the protein expressions after subretinal injection of AAV8 viruses with different promoters in mice.

As can be seen from FIG. 10A, at the time of 2 weeks after injection, the CMV promoter, CAG promoter, and EF1a promoter showed strong expressions, and the EFS promoter showed a weak EGFP intensity in the expression; wherein the expression sites of CMV promoter and CAG promoter were mainly in the RPE layer, inner segment, and outer segment, and the EF1a promoter and EFS promoter were expressed in the RPE layer, inner segment, outer segment, and outer nuclear layer.

Figure 10B:
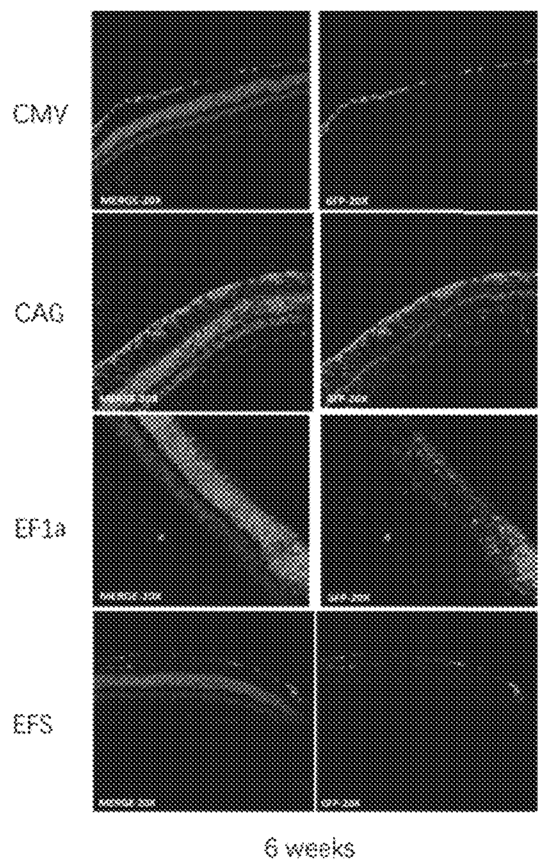

As can be seen from FIG. 10B, at the time of 6 weeks after injection, the CAG promoter and EF1a promoter showed strong expressions, and the CMV promoter and EFS promoter showed relatively weak EGFP intensities in the expression. Each of the promoters was expressed in the RPE layer, inner segment, outer segment, and outer nuclear layer.

Thus, the AAV8-CAG promoter had a more stable expression intensity and a wide expression range in mouse retina.

Example 13 Lipid Deposition after Infecting Cells with the Vector Comprising the Nucleic Acid Molecule in the Present Application The pAAV-CAG-CYP4V2 plasmid in Example 1 was packaged in accordance with the procedure in Example 9 to obtain the AAV8-CAG-CYP4V2 virus vector.

Figure 11A:
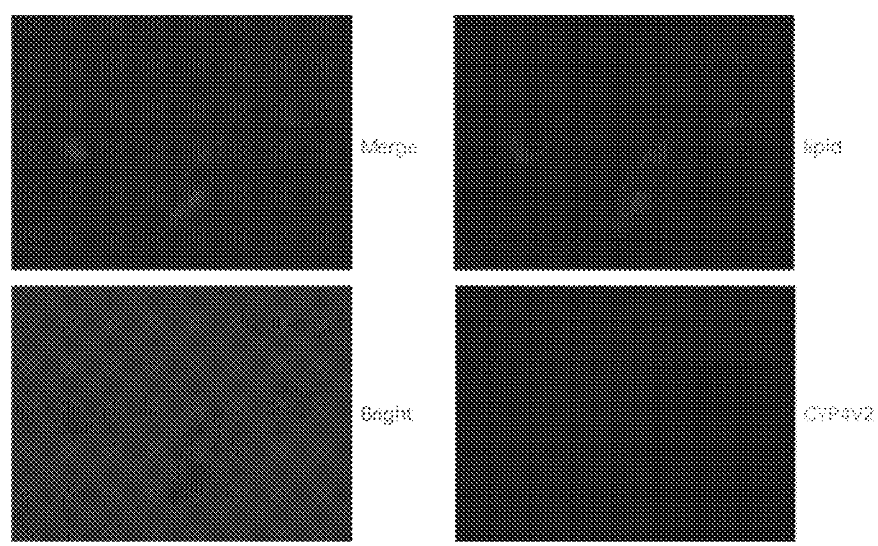
FIG. 11A shows the lipid deposition in the mock group CYP4V2 KO-ARPE19 cell line.
Figure 11B:
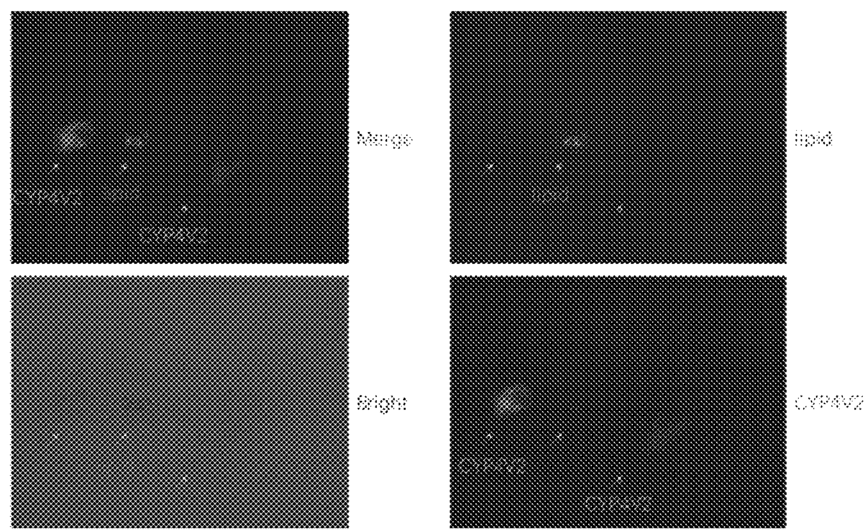
FIG. 11B shows the lipid deposition of CYP4V2 KO-ARPE19 cell line infected with AAV8-CAG-CYP4V2 viruses.
Figure 11C:
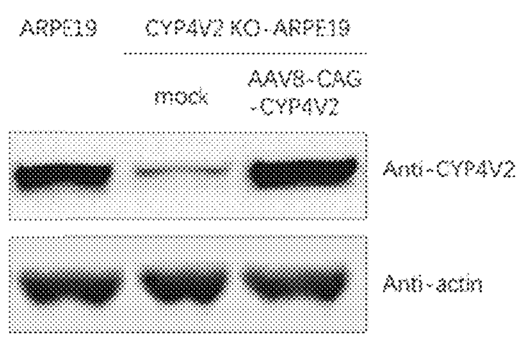
FIG. 11C shows the CYP4V2 expression in CYP4V2 KO-ARPE19 cell line infected with AAV8-CAG-CYP4V2 viruses and in wild-type ARPE19.

The CYP4V2 gene in the ARPE19 cell line (ATCC™, CRL-2302) was knocked out to construct a CYP4V2 KO-ARPE19 cell line (CRISPR-Cas9 knockout, targeting exon 2, sgRNA2: gcagatcattgagtacacag (SEQ ID NO: 22); sgRNA5: ccgacccagagcttcagcag (SEQ ID NO: 23)), and the cell line was infected with AAV8-CAG-CYP4V2. BODIPY (D3922, Thermo Fisher) was used to stain the neutral lipid, CYP4V2 antibody (Atlas™, HPA029122) was used to detect the CYP4V2 protein, and the lipid deposition and CYP4V2 protein expression were detected under a microscope. As can be seen from FIG. 11A-11C below, the AAV8-CAG-CYP4V2 virus infected the CYP4V2 KO-ARPE19 cell line. CYP4V2 showed detectable protein expression, and the lipid deposition of this cell line was reduced. Moreover, there was a negative correlation between lipid deposition and CYP4V2 protein expression.

Example 14 Lipid Deposition after Infecting iPSC-Derived RPE Cells from BCD Patients with the Vector Comprising the Nucleic Acid Molecule in the Present Application The BCD patients (genotype: CYP4V2: c.802-8_810del17bpinsGC homozygous mutation) were admitted to the Department of Ophthalmology, Peking University Third Hospital from November 2018 to December 2018. The Ethics Committee of Peking University Third Hospital approved all aspects of this study, and the informed consents for sample collection were obtained from the subjects (or their legal guardians).

Generation of human induced pluripotent stem cell (iPSC): The renal epithelial cells were extracted from urine using Urineasy Urinary Cell Separation Kit (Beijing Cellapy, CA3102500), and cultured and expanded using Urineasy Urinary Cell Expansion Kit (Beijing Cellapy, CA3103200), and the cells with 70-80% confluence at the 3rd to 4th passage were selected for the reprogramming experiment. The reprogramming experiment was performed using the hiPSC Reprogramming Kit (Beijing Cellapy, CA5002002), in accordance with the instructions of kit, to obtain human iPSCs which were used for the cell differentiation experiment.

RPEs were generated in accordance with Example 10.

Figure 12A:
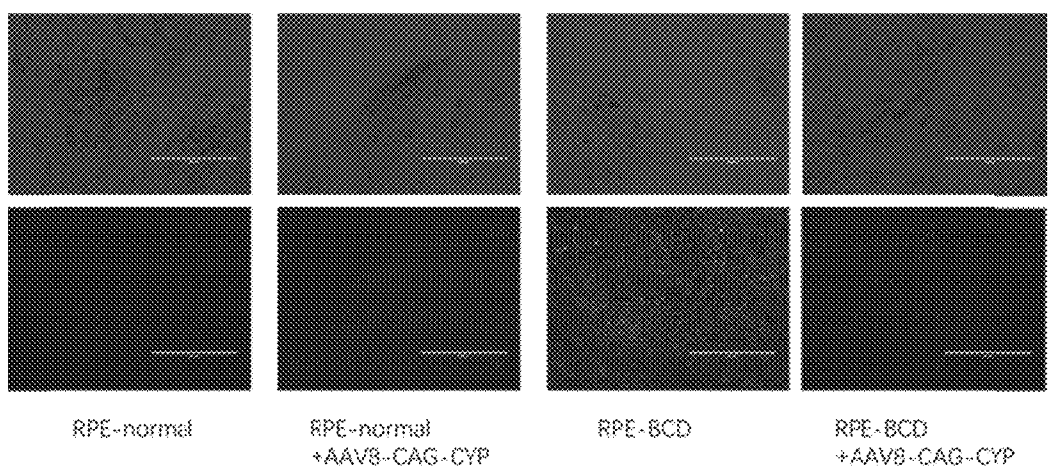
FIG. 12A shows the lipid deposition after infecting iPSC-induced RPE cells from healthy donors or BCD patients with AAV8-CAG-CYP4V2.

The same amount of RPEs from healthy donors or patients were infected with virus AAV8-CAG-CYP4V2 (MOI=$1\times10^6$). 10 days after infection, BODIPY (D3922, Thermo Fisher) was used to stain the neutral lipid, and the fluorescence signal was observed by fluorescence microscope (Life AMF4305). The results were shown in FIG. 12A. The RPE cells from healthy donors or patients in the infected or non-infected groups were lysed with RIPA lysis buffer, and the expression of CYP4V2 was detectable by western blotting (FIG. 12B).

Example 15 Infection of iPSC-Derived RPE Cells from BCD Patients with the Vector Comprising the Nucleic Acid Molecule in the Present Application and Detection of Cell Phagocytosis The generation, infection and western blotting detection for RPE cells were identical to those in Example 14. The latex beads (L4655, Sigma) were added to the cell culture medium, and the fluorescence signal was observed by fluorescence microscope (Life AMF4305) after 24 hours.

As can be seen from FIG. 13, the small number of fluorescent spots in the RPE-BCD group (the upper and lower images in the third column from the left) were free latex beads rather than latex beads entering the cells, and the fluorescent spots in every other image were latex beads phagocytosed by RPEs and thus entering the cells. Compared with RPEs from healthy donors, the ability of RPE cells from BCD patients to phagocytose latex beads was greatly weakened, while the infection with AAV8-CAG-CYP4V2 virus could restore the phagocytic ability of RPE cells from BCD patients to a certain extent and enhance the phagocytic ability of RPE cells from healthy donors.

Example 16 Treatment of BCD Model Mice with the Vector Comprising the Nucleic Acid Molecule in the Present Application 16.1 Generation and Detection of BCD Model Mice The BCD mice conformed to certain characteristics of BCD disease and served as a good animal model for studying the BCD disease. Through the subretinal injection in 1-month-old BCD mice (purchased from Biocytogen Pharmaceuticals (Beijing) Co., Ltd., Cyp4v3−/−), AAV8-CAG-CYP4V2 was delivered into the retina between RPE and outer segment, and the observation was performed after 3-6 months.

Process for subretinal injection: The experiment materials were prepared, the mice were subjected to mydriasis with 1% atropine, and then the mice were anesthetized by intraperitoneal injection of 80 mg/kg ketamine+8 mg/kg xylazine. After the anesthesia, the mice were subjected to mydriasis with 1% atropine again. Then the mice were placed in front of the animal experiment platform of the ophthalmic surgery microscope (Topcon, OMS800), and 0.5% proparacaine was dropped on the eyeballs of mice for local anesthesia. The fluorescein sodium stock solution was added to the virus at a concentration of fluorescein sodium: virus=1:100, and mixed by using a pipette. A minipore was pricked by insulin needle in advance in the ciliary pars plana of the mouse eyeball, through which a microsyringe needle passed to enter the vitreous chamber of the mouse eyeball. At this time, an appropriate amount of 2% hydroxymethyl cellulose was dropped on the mouse eyeball such that the mouse fundus can be seen under the microscope. Then the needle was inserted into the contralateral periphery retina while keeping off the lens. The viruses with sodium fluorescein were slowly pushed-in, with an injection volume of 1 μl in each eye and a virus concentration of $1\times10^9$ vg/μl. The fluorescein sodium served as the indicator for judging whether it was subretinal injected successfully, as shown in FIG. 14A. After the operation, the surface of the eyeball was washed with normal saline and the mouse was placed in a cage to wait for waking up. FIG. 14A showed a photograph of the subretinal injections of mice under a microscope.

16.2 Observation of the Crystalline Deposition by In Vivo Fundus Photography 3 or 6 months after the injection of AAV8-CAG-CYP4V2, the mice were subjected to mydriasis with 1% atropine, and then the mice were anesthetized by intraperitoneal injection of 80 mg/kg ketamine+8 mg/kg xylazine. The anesthetized mice were held flat on the experiment platform of Micro III small animal retinal imaging system (Phoenix Research Laboratory, Micro III), and an appropriate amount of 2% hydroxymethyl cellulose was dropped on the mouse eyeball to improve the contact effect between the lens and the cornea. The positions of the eyes in mice were adjusted by lifting and rotating the experiment platform, and the focal length and light intensity were adjusted to obtain the fundus images of mice, which were taken by the Micro III software. After the photography was completed, the quantitative analysis on crystalline deposition was performed using GraphPad Prism software.

Figure 14B:
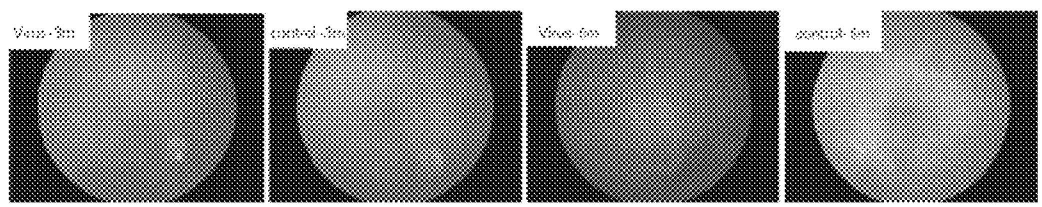
FIG. 14B shows the crystalline deposition by fundus photography at 3 months and 6 months after injecting AAV8-CAG-CYP4V2 into BCD mice.

The results were shown in FIG. 14B, indicating that the fundus crystalline deposition was relieved after the injection of AAV8-CAG-CYP4V2.

16.3 Morphological Observation of Retinal Tissue

Fixation and dehydration: the mice injected with AAV8-CAG-CYP4V2 were sacrificed by cervical dislocation and the eyeballs were extracted. The mouse eyeball was placed in a 1.5 ml EP tube, and immersed in 1 ml of 4% paraformaldehyde at 4° C. overnight. Then the eyeball was transferred into a new 1.5 ml EP tube containing 1 ml of 30% sucrose solution for dehydration, until the eyeball sank to the bottom. Then the mouse eyeball was placed into another 1.5 ml EP tube containing optimal cutting temperature compound (OCT). The mouse eye was positioned by tweezer to look straight ahead. The EP tube was capped and placed in liquid nitrogen. After being completely frozen, the frozen sections were obtained, with a section thickness of 7 μm. After fixation in acetone at 4° C. for 10 min, they were stored at −80° C. The sections were taken out, and after recovery to room temperature, washed with PBS for 3 times (each for 5 min). The parts without tissues in the glass slide were wiped up. After 40 μl of blocking solution (5% donkey serum) were dropped onto each glass slide, the glass slide was blocked at room temperature for 1 h. The primary antibody was diluted with 5% donkey serum. About 40 μl of antibody working solution was dropped to completely cover the mouse eyeball tissues for incubating at 4° C. overnight. The primary antibody used in this experiment was: CYP4V2 (1:50, purchased from Sigma). The glass slide was taken out and washed with PBS for 3 times (each for 5 min). The secondary antibody (purchased from Thermo Fisher Scientific) was diluted with PBS at a ratio of 1:800. About 40 μl of secondary antibody working solution was dropped to completely cover the mouse eyeball tissues for incubating at room temperature for 1 h. The glass slide was washed with PBS for 3 times, and DAPI diluent (1:5000) was added for incubating at room temperature for 15 min. After the anti-fluorescence-quenching mounting medium was dropped, the glass slide was covered with a coverslip, and stored at −20° C. in dark. The Nikon A1 laser confocal microscope equipped with NIS-Elements C software was used for observation and imaging.

Figure 15:
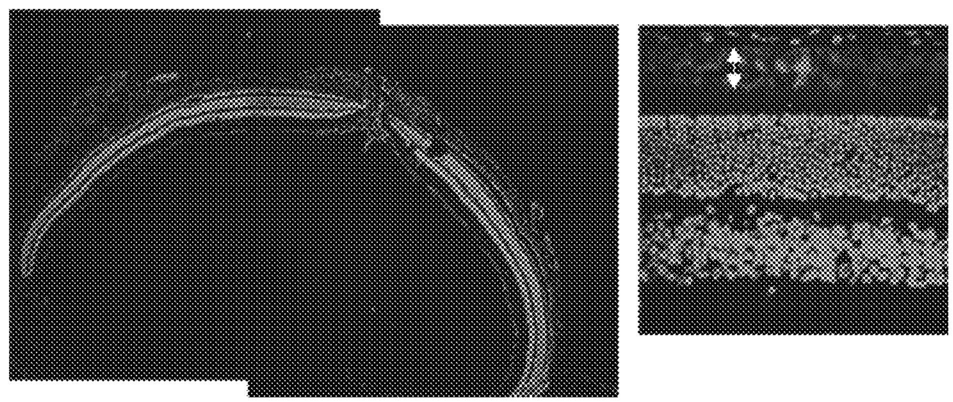
FIG. 15 shows the CYP4V2 expression after injecting AAV8-CAG-CYP4V2 into BCD mice.

The results were shown in FIG. 15, indicating the expression of hCYP4V2 after the subretinal injection of AAV8-CAG-CYP4V2 in mice (double arrows indicate the range in the figure).

16.4 Improvement of ERG Level in Mice

Dark adaptation of mice after unilateral subretinal injection of AAV8-CAG-CYP4V2: the mice were subjected to the dark adaptation for at least 16 hours, after which all the operations were performed under dark red light. Anesthesia in mice: the anesthesia was performed by intraperitoneal injection of 80 mg/kg ketamine+8 mg/kg xylazine. After the anesthesia was completed, the mice were subjected to mydriasis with 1% atropine under the illumination of dark red light. The mice were fixed with adhesive tape in front of the animal experiment platform of the visual electrophysiology instrument Espion E2, and the eyes were consistent and fully exposed. The ground electrode needle was inserted into the root of the mouse tail, and the reference electrode needle was inserted into the mouse jaw. Two gold ring recording electrodes were clamped on the electrode holder of the animal experiment platform, and their angles were adjusted so that they slightly touched the top end in the center of the left and right corneas, respectively. An appropriate amount of 2% hydroxymethyl cellulose was dropped to improve the contact effect between the gold ring electrode and the cornea. The information about mouse number and age was entered in the Espion E2 computer system and then the program was run. The dark-adaptation flash intensity was 0.003, 0.01, 0.1, 1, 3, 10, and 100 cd·s/m$^2$, respectively (the background light intensity was 0 cd·s/m$^2$, the stimulation interval was 15 s, and the average of three ERG signals was recorded); and the light-adaptation flash intensity was 3, 10, 30, and 100 cd·s/m$^2$, respectively (the light-adaptation time was 5 min, the background light intensity was 30 cd·s/m$^2$, the stimulation interval was 15 s, and the average of five ERG signals was recorded). After the program was completed, the running results were automatically saved, and GraphPad Prism was used for the result statistics. The side injected with the virus was the virus group, and the side not injected with the virus was the control group. Statistical analysis: two-tailed paired t-test. *P<0.05, P<0.01, *P<0.005. Error bars: standard error.

Figure 16:
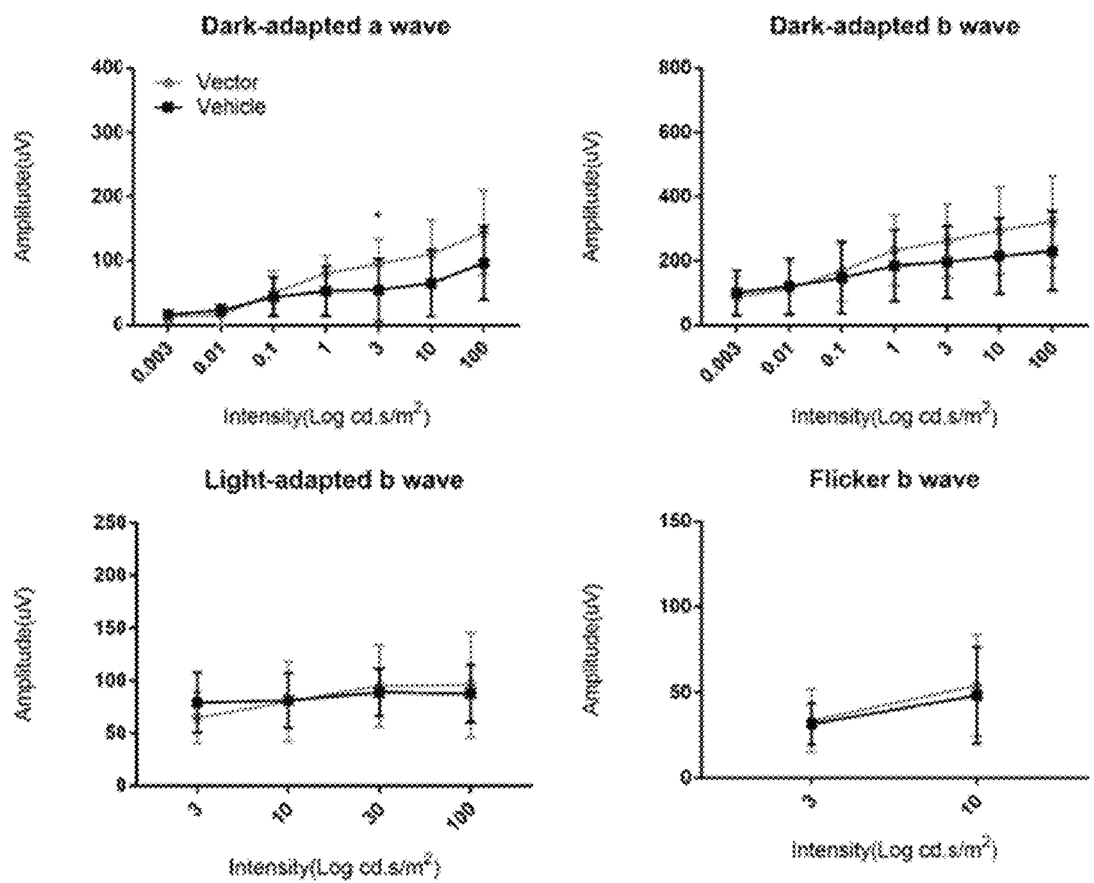
FIG. 16 shows the REG levels at 3 months after injecting AAV8-CAG-CYP4V2 into BCD mice.
Figure 17:
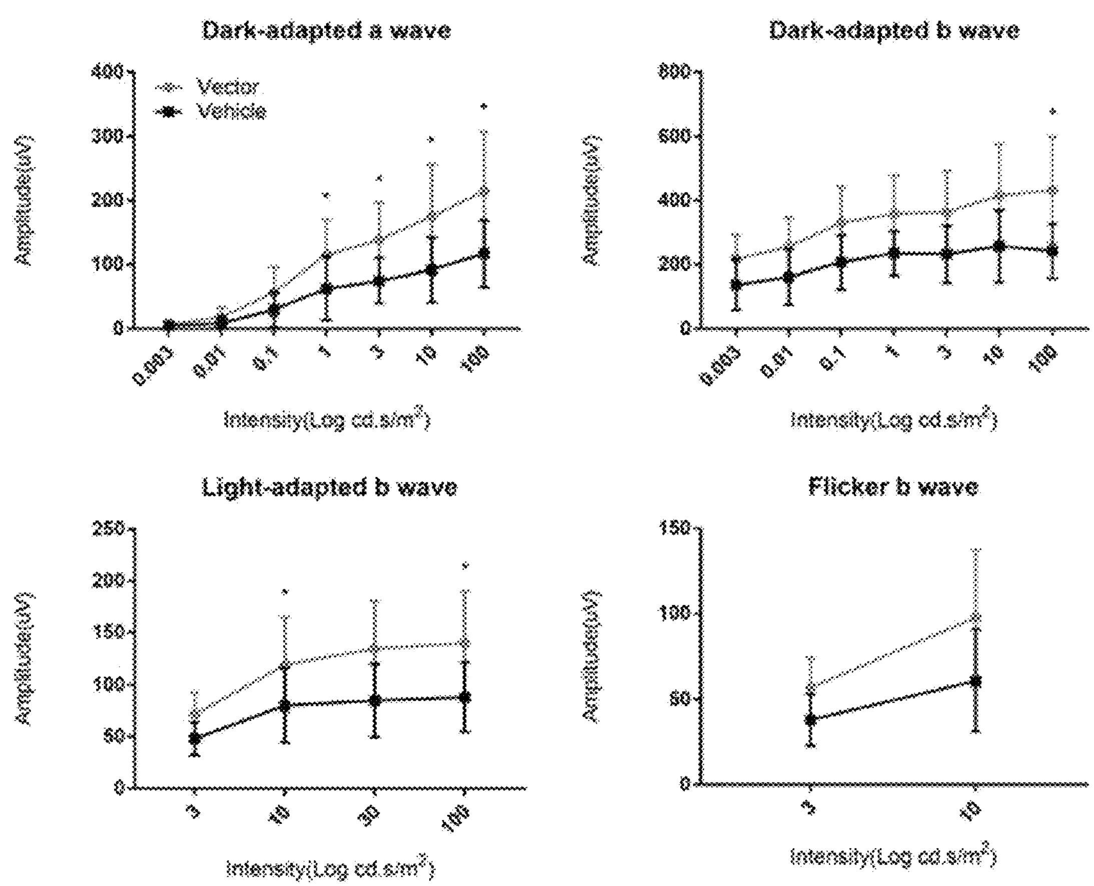
FIG. 17 shows the REG levels at 6 months after injecting AAV8-CAG-CYP4V2 into BCD mice.
Figure 18:
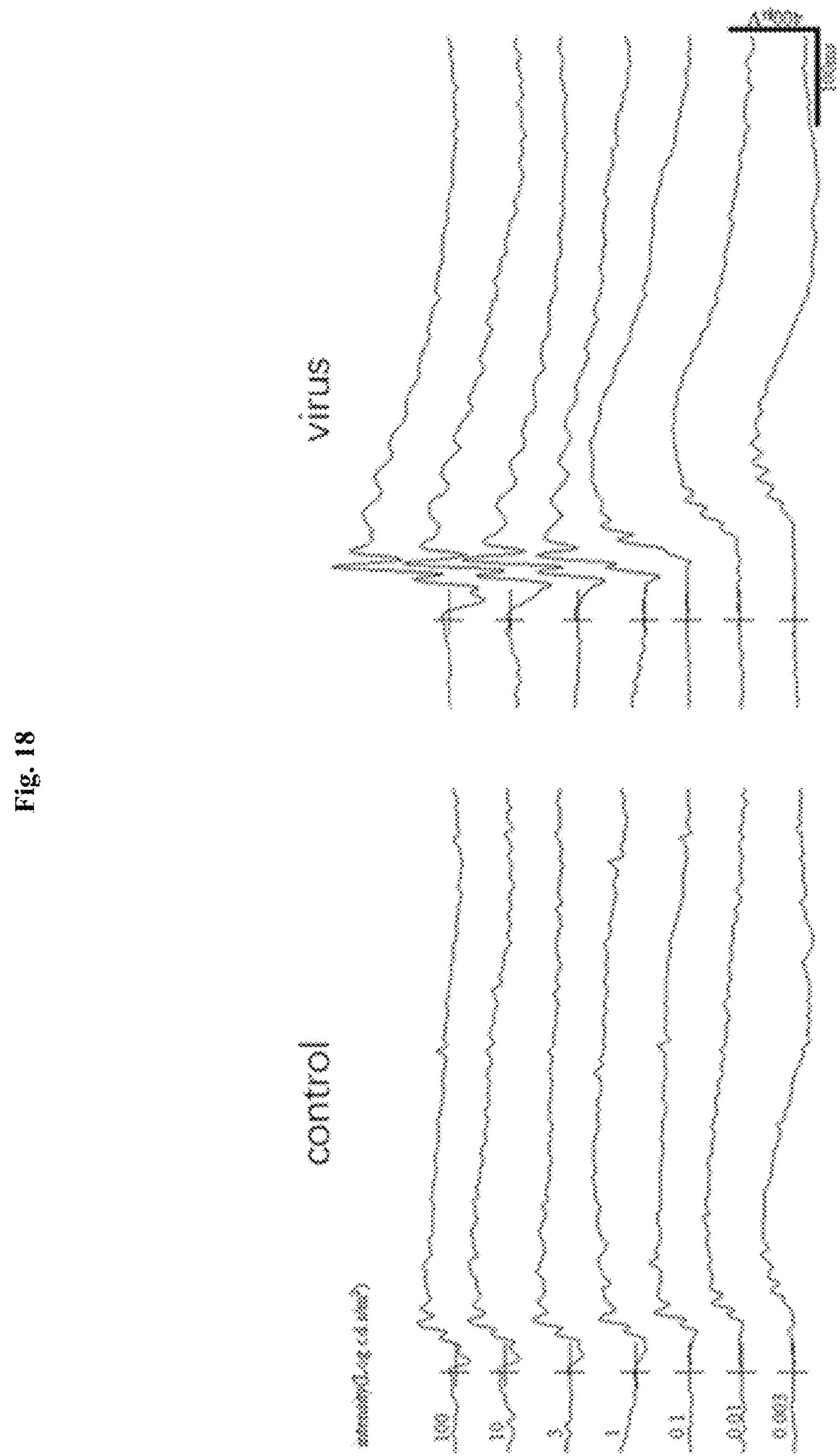
FIG. 18 shows the ERG dark response b wave at 6 months after injecting AAV8-CAG-CYP4V2 into BCD mice.
Figure 19:
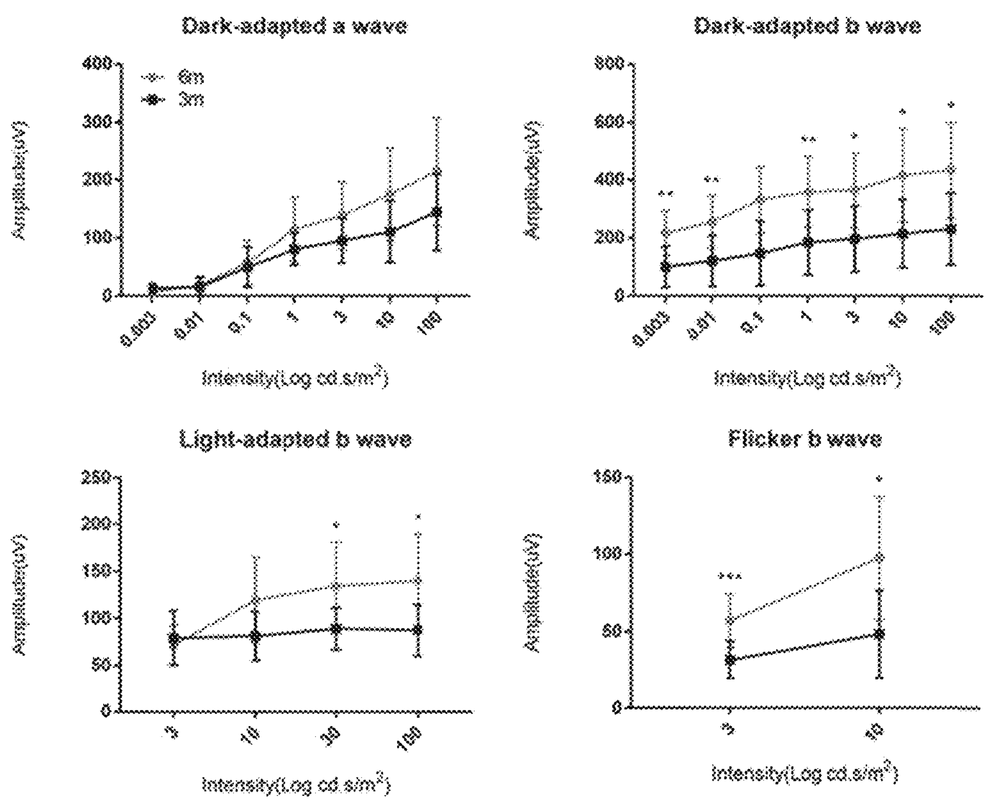
FIG. 19 shows the REG levels at 3 months and 6 months after injecting AAV8-CAG-CYP4V2 into BCD mice.

The results were shown in FIGS. 16 to 19. The unilateral eyes of Cyp4v3 KO mice were injected with viruses, and 3 months after treatment, ERG (n=8) in the treated eyes (virus group) had no significant change in the amplitude of each wave compared with the control eyes (control group) (FIG. 16). At 6 months after treatment, the overall amplitude of ERG (n=8) in the treated eyes (virus group) was higher than that of the control eyes (control group), and the difference in the amplitude change under individual light intensity stimulation was statistically significant (FIG. 16). After treatment for 6 months, the dark response b wave of ERG was significantly higher in the treated eyes (virus group, FIG. 17) than in the control eyes (control group, FIG. 18). By comparing the ERG conditions at 3 months and 6 months after treatment, the amplitude of the treated eyes of mice at 6 months after treatment was significantly higher than that at 3 months after treatment (FIG. 19).

16.5 Detection of the Cell Number and Morphology by Mouse Eyeball RPE Flattening and Staining The pre-chilled PBS was added to a 1.5 ml EP tube. After the mice were sacrificed, the eyeballs of the mice were extracted and immersed in PBS for 15 min. The mouse eyeball was transferred to a new 1.5 ml EP tube containing 1 ml of 4% paraformaldehyde, and fixed for 1 h. The anterior segment of the mouse eyeball was removed under a stereomicroscope (Olympus, SZ61-SET), the neural retinal layer was separated from the RPE layer, and the RPE layer was cut into 4 flaps. The RPE flatmount was washed in the pre-chilled PBS for 3 times (each for 5 min). The RPE flatmount was permeabilized in 0.1% Triton for 20 min, then washed with PBS for 3 times (each for 5 min). The RPE flatmount was placed onto one well of a 96-well plate, and incubated at room temperature for 1 h after the Phalloidin working solution diluted with PBS at a ratio of 1:200 was added. The RPE flatmount was washed with PBS for 3 times (each for 5 min), flatten on a glass slide which was then mounted by a coverslip after dropping a small amount of mounting medium, and observed under Nikon fluorescence microscope.

Figure 20:
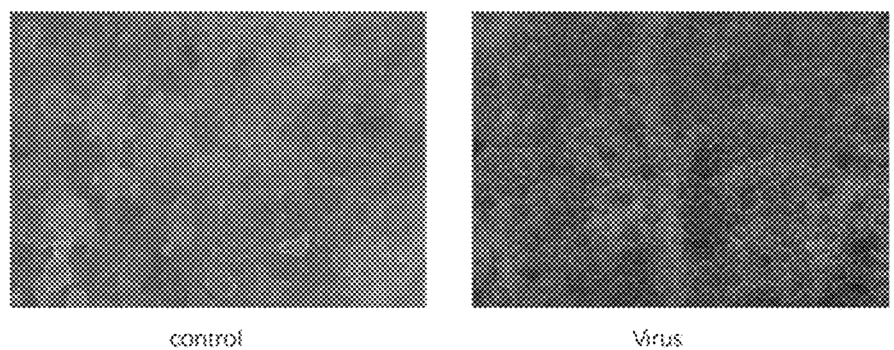
FIG. 20 shows the morphology improvement and number maintenance for RPE cells after the treatment in BCD mice for 6 months.

The results were shown in FIG. 20. Compared with the control BCD mice not injected with viruses (left), the RPE cells had more intact hexagonal morphology and dense arrangements in BCD mice injected with viruses. Moreover, the numbers of RPE cells in the same area in the virus group was larger than that in the control group.

Example 17 Production of AAV Vector Comprising the Nucleic Acid Molecule in the Present Application The AAV vector was produced using the Helper-free packaging system (synthesized by Genewiz Inc., Suzhou, China).

Using *E. coli* fermentation under GMP conditions, three plasmids for AAV packaging were obtained, namely ZY04 (helper plasmid for AAV Helper-free packaging system, providing the Ad5 adenovirus genes E2A, E4, and VA RNA genes necessary for AAV packaging), ZY05 (serotype plasmid for AAV packaging, mainly providing REP2 and CAP8 genes for AAV packaging), and ZY06 (target gene plasmid, containing the nucleic acid molecule in the present application). Three *E. coli* fermentation broths were used to obtain three plasmids for AAV packaging, through the steps of strain library establishment, fermentation culture, collection of bacteria, lysis, clarification and filtration, chromatography, ultrafiltration, filtration, and filling.

HEK293 cells were transfected with PEI under GMP conditions to obtain AAV vectors, and the main procedure was as follows: cell recovery, proliferation, transfection, harvesting, clarification and filtration, affinity chromatography, anion chromatography, ultrafiltration, filtration, and filling.

Example 18 Treatment of BCD Patients with the Vector Comprising the Nucleic Acid Molecule in the Present Application 18.1 Indication Population:

Patients were diagnosed with biallelic CYP4V2 mutations by gene sequencing and clinically diagnosed with BCD disease (patient 001 and patient 003, Beijing Tongren Hospital affiliated to Capital Medical University).

18.2 Route of Administration:

AAV8-CAG-CYP4V2 (ZVS101e) was administrated by subretinal injection, with a dosing volume of 50 μl-300 μl and a dosage of $1\times10^{10}$ vg/eye-$1\times10^{12}$ vg/eye.

18.3 Efficacy Evaluation:

All the subjects had no drug-related serious adverse reactions, indicating that ZVS101e has a good clinical safety. Meanwhile, the subjects had improved visual functions, with significantly improved indicators such as best corrected visual acuity (BCVA) (Chaikitmongkol, V., et al. (2018). "Repeatability and Agreement of Visual Acuity Using the ETDRS Number Chart, Landolt C Chart, or ETDRS Alphabet Chart in Eyes With or Without Sight-Threatening Diseases." *JAMA Ophthalmol* 136(3): 286-290), and multi-luminance mobility test (MLMT) (Chung, D. C., et al. (2018). "Novel mobility test to assess functional vision in patients with inherited retinal dystrophies." *Clin Exp Ophthalmol* 46(3): 247-259), indicating that ZVS101e had a good clinical efficacy.

Figure 21:
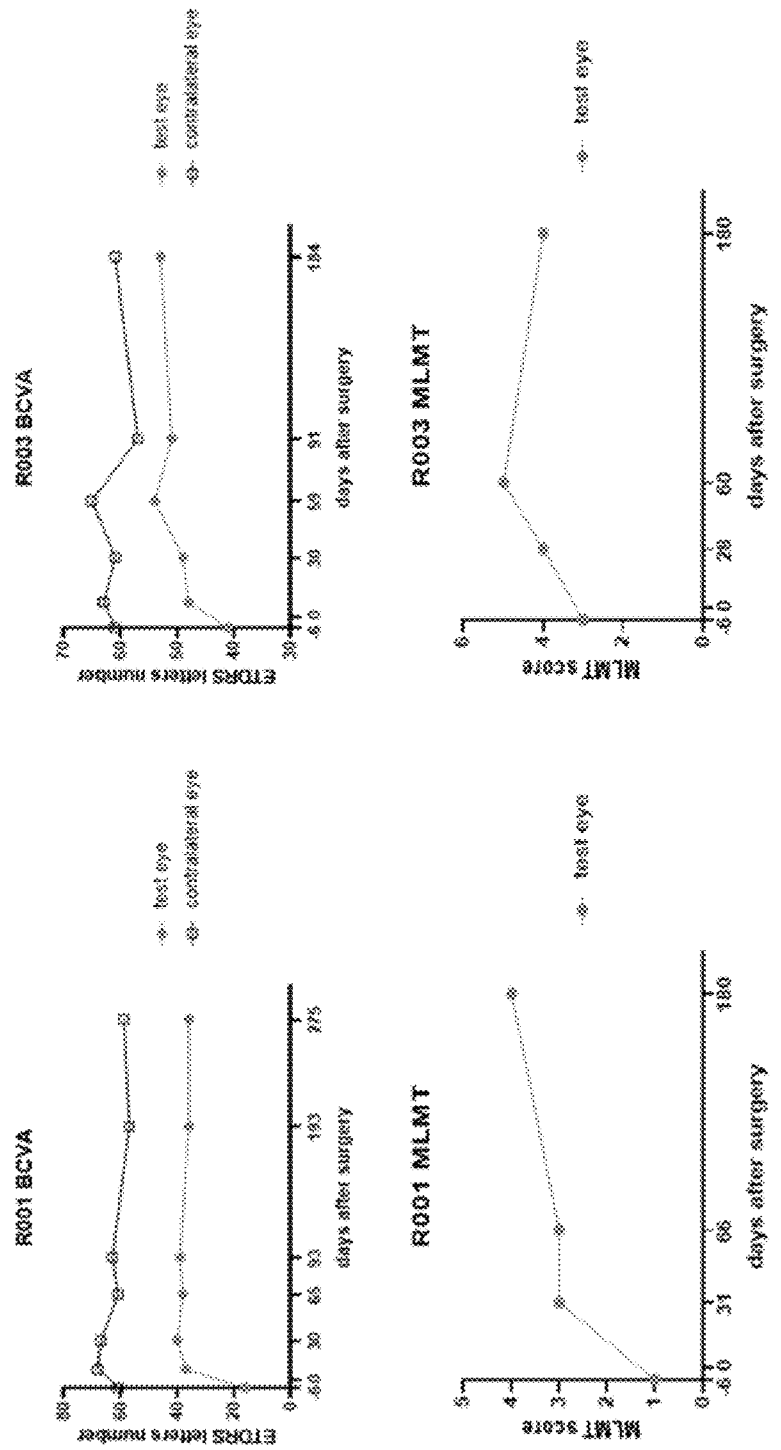
FIG. 21 shows the efficacy of AAV8-CAG-CYP4V2 (ZVS101e) subretinal injection in BCD patients.

The central visual acuities of patients at baseline and different time points after treatment were detected by ETDRS visual chart. The BCVA and MLMT scores of patients 001 and 003 at baseline and after treatment were shown in FIG. 21.

What is claimed is:

1. A vector comprising a polynucleotide encoding CYP4V2 and a promoter operably linked to the polynucleotide encoding CYP4V2; wherein the vector comprises the entire nucleotide sequence set forth in SEQ ID NO: 11; and wherein the vector is a recombinant AAV2/8 vector.

2. The vector according to claim 1, wherein the vector further comprises a polyadenylation (PolyA) signal site located at 3' end of the polynucleotide encoding CYP4V2, wherein the polyadenylation (PolyA) signal site comprises an entire nucleotide sequence set forth in SEQ ID NO: 3; and/or the promoter is located at 5' end of the polynucleotide encoding CYP4V2.

3. A cell comprising the vector according to claim 1.

4. A pharmaceutical composition comprising: a) the vector according to claim 1, and b) a pharmaceutically acceptable adjuvant.

5. The pharmaceutical composition according to claim 4, wherein the adjuvant includes stabilizer, excipient, diluent, solubilizer, surfactant, emulsifier, preservative, or any combination thereof.

6. A kit comprising: a) the vector according to claim 1, and b) helper plasmids or helper viruses that provide helper functions for virus packaging.

7. A method for treating or alleviating Bietti's crystalline dystrophy (BCD), comprising administrating the vector according to claim 1 to a subject in need thereof, wherein the administration is subretinal injection.

8. The method according to claim 7, wherein the dosing volume is from 50 μl to 300 μl, and/or the dosage is from $1\times10^{10}$ vg/eye to $1\times10^{12}$ vg/eye.

9. The method according to claim 7, wherein the subject is human.

* * * * *